US009896492B2

(12) United States Patent
Nakamura et al.

(10) Patent No.: US 9,896,492 B2
(45) Date of Patent: Feb. 20, 2018

(54) HJURP PEPTIDES AND VACCINES INCLUDING THE SAME

(71) Applicant: OncoTherapy Science, Inc., Kanagawa (JP)

(72) Inventors: Yusuke Nakamura, Tokyo (JP); Takuya Tsunoda, Kanagawa (JP); Ryuji Ohsawa, Kanagawa (JP); Sachiko Yoshimura, Kanagawa (JP); Tomohisa Watanabe, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 0 days.

(21) Appl. No.: 15/197,278

(22) Filed: Jun. 29, 2016

(65) Prior Publication Data

US 2016/0368958 A1   Dec. 22, 2016

Related U.S. Application Data

(62) Division of application No. 14/205,163, filed on Mar. 11, 2014, now Pat. No. 9,403,890, which is a division of application No. 13/583,195, filed as application No. PCT/JP2011/001407 on Mar. 10, 2011, now Pat. No. 8,933,014.

(60) Provisional application No. 61/312,931, filed on Mar. 11, 2010, provisional application No. 61/315,320, filed on Mar. 18, 2010.

(51) Int. Cl.
| | | |
|---|---|---|
| *A61K 39/00* | (2006.01) |
| *C07K 14/47* | (2006.01) |
| *C07K 7/06* | (2006.01) |
| *C07K 16/18* | (2006.01) |
| *A61K 35/12* | (2015.01) |
| *A61K 38/00* | (2006.01) |

(52) U.S. Cl.
CPC ............ *C07K 14/4748* (2013.01); *C07K 7/06* (2013.01); *C07K 16/18* (2013.01); *A61K 35/12* (2013.01); *A61K 38/00* (2013.01); *A61K 39/00* (2013.01)

(58) Field of Classification Search
CPC ................................................. C07K 14/4748
See application file for complete search history.

(56) References Cited

U.S. PATENT DOCUMENTS

| 7,514,084 | B2 | 4/2009 | Tahara et al. |
| 2006/0024692 | A1 | 2/2006 | Nakamura et al. |
| 2006/0051746 | A1 | 3/2006 | Chisari |
| 2007/0036812 | A1 | 2/2007 | Sato et al. |

FOREIGN PATENT DOCUMENTS

| CN | 1849395 A | 10/2006 |
| EP | 2 360 173 A1 | 8/2011 |
| JP | 2004-000216 A | 1/2004 |
| JP | 2006/052216 A | 2/2006 |
| RU | 2367468 C2 | 9/2009 |
| WO | 2004/024766 A1 | 3/2004 |
| WO | 2004/031413 A2 | 4/2004 |
| WO | 2005/049073 A2 | 6/2005 |
| WO | 2006-009920 A2 | 1/2006 |
| WO | 2008/020653 A1 | 2/2008 |
| WO | 2008/126413 A1 | 10/2008 |
| WO | 2010/037124 A1 | 4/2010 |
| WO | 2010-061919 A1 | 6/2010 |
| WO | 2010-106770 A1 | 9/2010 |
| WO | 2010-113495 A1 | 10/2010 |
| WO | 2004/108948 A | 12/2016 |

OTHER PUBLICATIONS

Bai et al., "Antigenic Drift as a Mechanism for Tumor Evation of Destruction by Cytolytic T Lymphocytes," J. Clin. Invest. vol. 111, No. 10, pp. 1487-1496 (May 2003).
Singh et al., "Immunoediting Sculpts Tumor Epitopes During Immunotherapy," Cancer Res., Mar. 1, 2007, 67:(5), pp. 1887-1892.
Adams, et al. "Prediction of binding to MHC class I molecules," *J Immunol Methods*, vol. 185(2), pp. 181-190 (Sep. 25, 1995).
Belli, et al., "Vaccination of Metastatic Melanoma Patients With Autologous Tumor-Derived Heat Shock Protein gp96-Peptide Complexes: Clinical and Immunologic Findings," *J Clin Oncol.*, vol. 20(20), pp. 4169-4180 (Oct. 15, 2002).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).

(Continued)

*Primary Examiner* — Prema Mertz
(74) *Attorney, Agent, or Firm* — Kilpatrick Townsend & Stockton LLP

(57) ABSTRACT

Isolated peptides derived from SEQ ID NO: 50 and fragments thereof that bind to an HLA antigen and induce cytotoxic T lymphocytes (CTL) and thus are suitable for use in the context of cancer immunotherapy, more particularly cancer vaccines are described herein. The inventive peptides encompasses both the above mentioned amino acid sequences and modified versions thereof, in which one, two, or several amino acids sequences substituted, deleted, added or inserted, provided such modified versions retain the requisite cytotoxic T cell inducibility of the original sequence. Further provided are nucleic acids encoding any of the aforementioned peptides as well as pharmaceutical agents, substances and/or compositions that include or incorporate any of the aforementioned peptides or nucleic acids. The peptides, nucleic acids, pharmaceutical agents, substances and compositions of this invention find particular utility in the treatment of cancers and tumors, including, for example, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

9 Claims, 9 Drawing Sheets

(56) References Cited

OTHER PUBLICATIONS

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al., "Cytolytic T-cell responses of cancer patients vaccinated with a MAGE antigen," *Immunol Rev.*, vol. 188, pp. 33-42 (Oct. 2002).
Daigo, et al., "Activation of HJURP involved in the chromosomal stability and immortality of cancer cells," *Nihon Gangakkai Sokai Shouroku*, 66:133, IS5-4, 1 page (2007).
Dionne, et al., "Functional characterization of CTL against gp100 altered peptide ligands," *Cancer Immunol Immunother.*, vol. 52(4), pp. 199-206 (Apr. 2003, Epub Feb. 18, 2003).
Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Dunleavy, et al., "HJURP is a Cell-Cycle-Dependent Maintenance and Deposition Factor of CENP-A at Centromeres", *Cell*, vol. 137, No. 3, pp. 485-497 (2009).
Falk, et al., "Allele-specific motifs revealed by sequencing of self-peptides eluted from MHC molecules," *Nature*, vol. 351(6324), pp. 290-296 (May 23, 1991).
Foltz, et al., "Centromere-Specific Assembly of CENP-A Nucleosomes Is Mediated by HJURP", *Cell*, vol. 137, No. 3, pp. 472-484 (2009).
Frankel, et al., "Characterization of diphtheria fusion proteins targeted to the human interleukin-3 receptor," *Protein Eng.*, vol. 13(8), pp. 575-581 (Aug. 2000).
Fujie, et al., "A Mage-1-Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Hoffmann, et al., "The Ability of Variant Peptides to Reverse the Nonresponsiveness of T Lymphocytes to the Wild-Type Sequence p53$_{264-272}$ Epitope," *J Immunol.*, vol. 168(3), pp. 1338-1347 (Feb. 1, 2002).
Hu, et al., "The expression level of HJURP has an independent prognostic impact and predicts the sensitivity to radiotherapy in breast cancer," *Breast Cancer Res.*, vol. 12(2), R18, 15 pages (2010, Epub Mar. 8, 2010).
Isogai, T., et al., "Hypothetical protein FLJ90328 (Fetal liver expressing gene 1)," Database DDBJ/EMBL/GenBank[online], Accession No. Q8NCD3, 12 pgs. (01 Fed 2005, updated Jul. 11, 2012) http://www.ncbi.nlm.nih.gov/protein/74715192?sat=CAGE&satkey=562244.
Kamiya, K., et al., "Division of Genome Biology Department of Experimental Oncology," *Proc. Hiroshima Univ. RIRBM*, vol. 44, pp. 273-280 (2003).
Kato, T., et al., "Activation of Holliday Junction-Recognizing Protein Involved in the Chromosomal Stability and Immortality of Cancer Cells," *Cancer Research*, vol. 67(18), pp. 8544-8553 (2007).
Kikuchi, et al., "Identification of a Sart-1-Derived Peptide Capable of Inducing HLA-A24-Restricted and Tumor-Specific Cytotoxic T Lymphocytes," *Int J Cancer*, vol. 81(3), pp. 459-466 (May 5, 1999).
Kondo, et al., "Prominent Roles of Secondary Anchor Residues in Peptide Binding to HLA-A24 Human Class I Molecules," *J Immunol.*, vol. 155(9), pp. 4307-4312 (Nov. 1, 1995).
Kubo, et al., "Definition of Specific Peptide Motifs for Four Major HLA-A Alleles," *J Immunol.*, vol. 152(8), pp. 3913-3924 (Apr. 15, 1994).
Murray, et al., "Biochemistry of Human", Moscow: Mir.,1:34 with English translation (1993).
Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).
Pakula, et al., "Genetic Analysis of Protein Stability and Function," *Annu Rev Genet.*, vol. 23, pp. 289-310 (1989).
Parker, et al., "Scheme for Ranking Potential HLA-A2 Binding Peptides Based on Independent Binding of Individual Peptide Side-Chains," *J Immunol.*, vol. 52(1), pp. 163-175 (Jan. 1, 1994).
Rammensee, et al., "MHC ligands and peptide motifs: first listing," *Immunogenetics*, vol. 41(4), pp. 178-228 (1995).
Rosenberg, et al., "Cancer Immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Stevanovic, "Identification of Tumour-Associated T-Cell Epitopes for Vaccine Development", *Nat Rev Cancer*, vol. 2(7):514-520 (2002).
Suda, et al., "Identification of secernin 1 as a novel immunotherapy target for gastric cancer using the expression profiles of cDNA microarray," *Cancer Sci.*, vol.97(5), pp. 411-419 (May 2006).
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphoctes," *Cancer Res.*, vol. 59(21), pp. 5554-5559 (Nov. 1, 1999).
Watanabe, et al., "Identification of immunoglobulin superfamily 11 (IGSF11) as a novel target for cancer immunotherapy of gastrointestinal and hepatocellular carcinomas," *Cancer Sci.*, vol. 96(8), pp. 498-506 (Aug. 2005).
Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
Database Genbank, NP115581.3, downloaded from http://www.ncbi.nlm.nih.gov/protein/NP_115581.3, 2 pages (downloaded Nov. 3, 2012).
Database Uniprot/Swiss-Prot, Q8NCD3, 9 pages, (last modified Oct. 19, 2011).

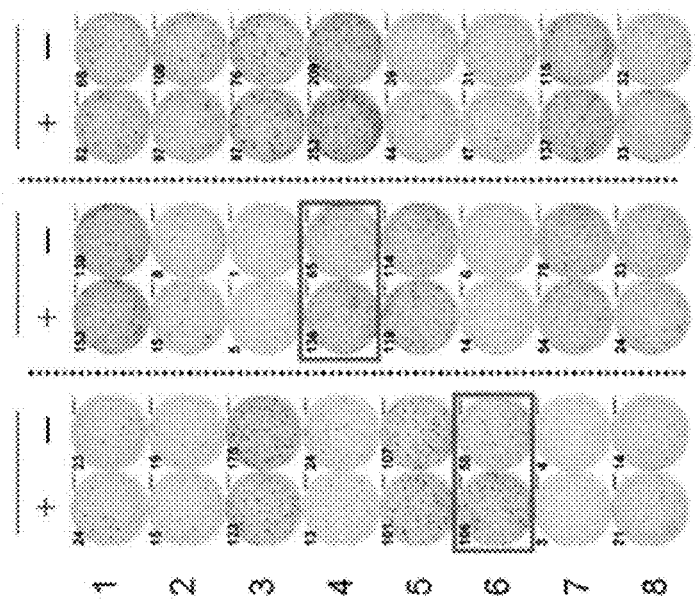
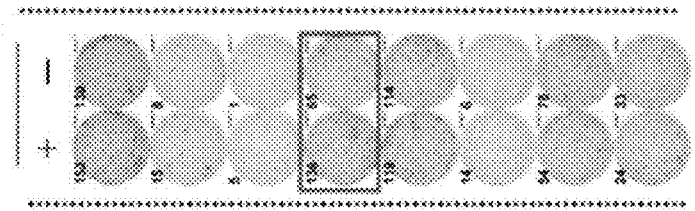
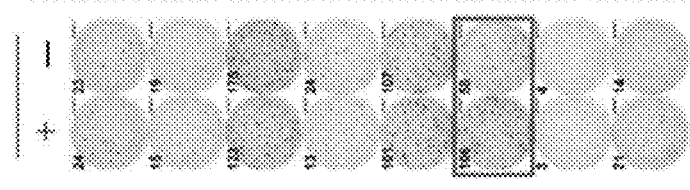
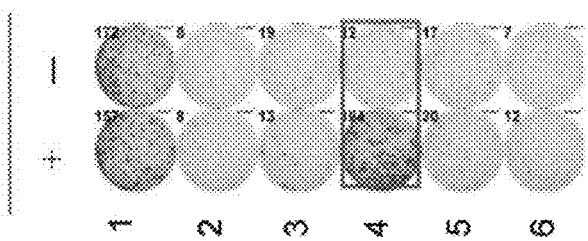
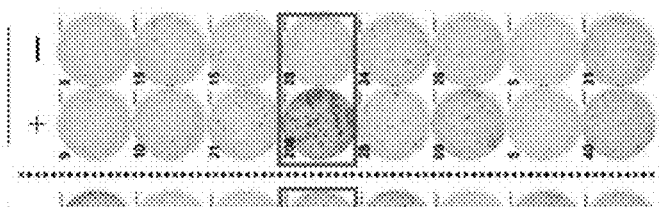
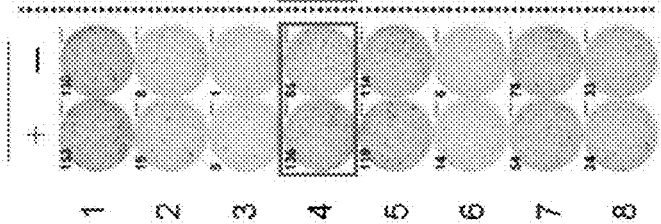
Fig. 1F HJURP-A24-9-149
Fig. 1E HJURP-A24-10-162
Fig. 1D HJURP-A24-10-383
Fig. 1C HJURP-A24-9-408
Fig. 1B HJURP-A24-9-263
Fig. 1A HJURP-A24-9-28

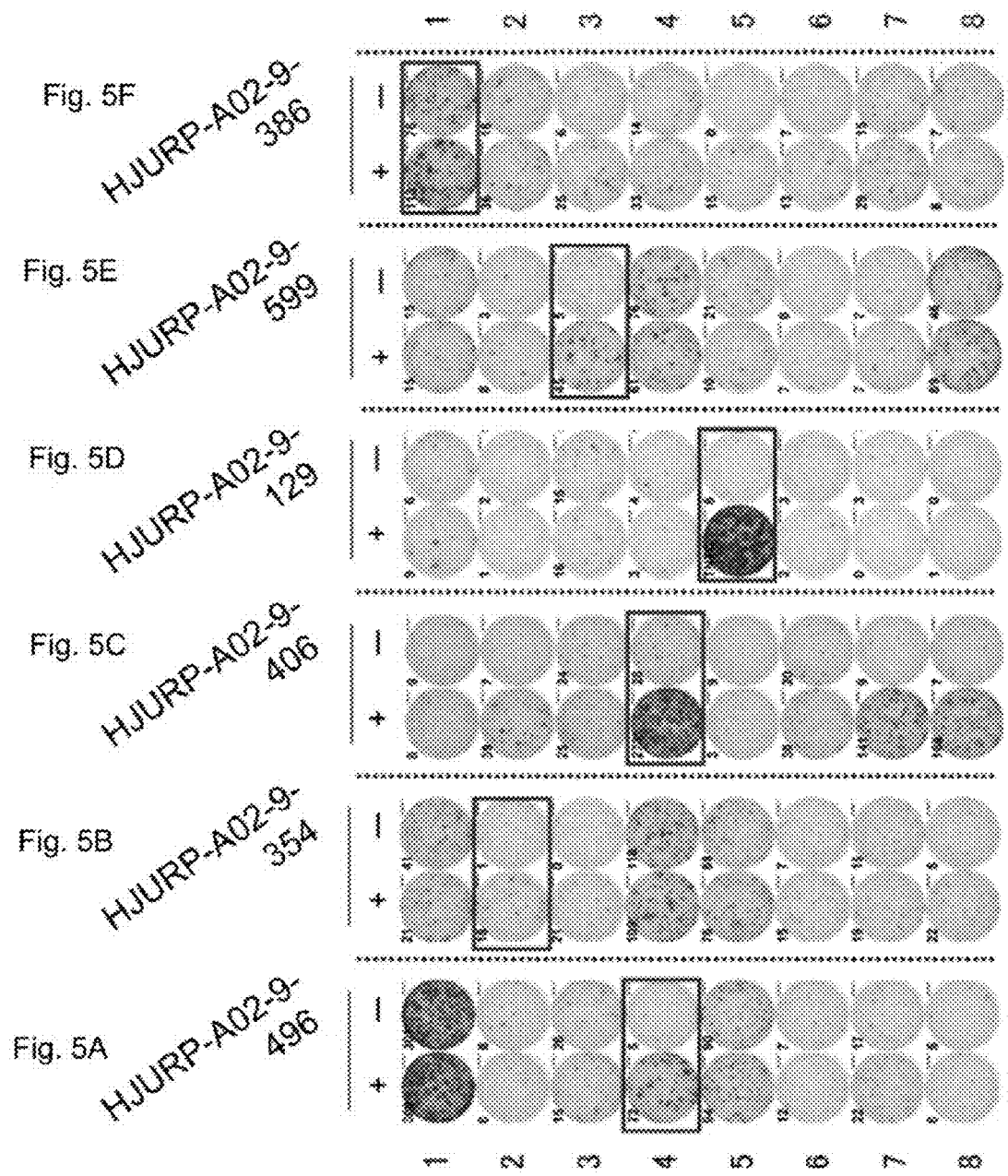

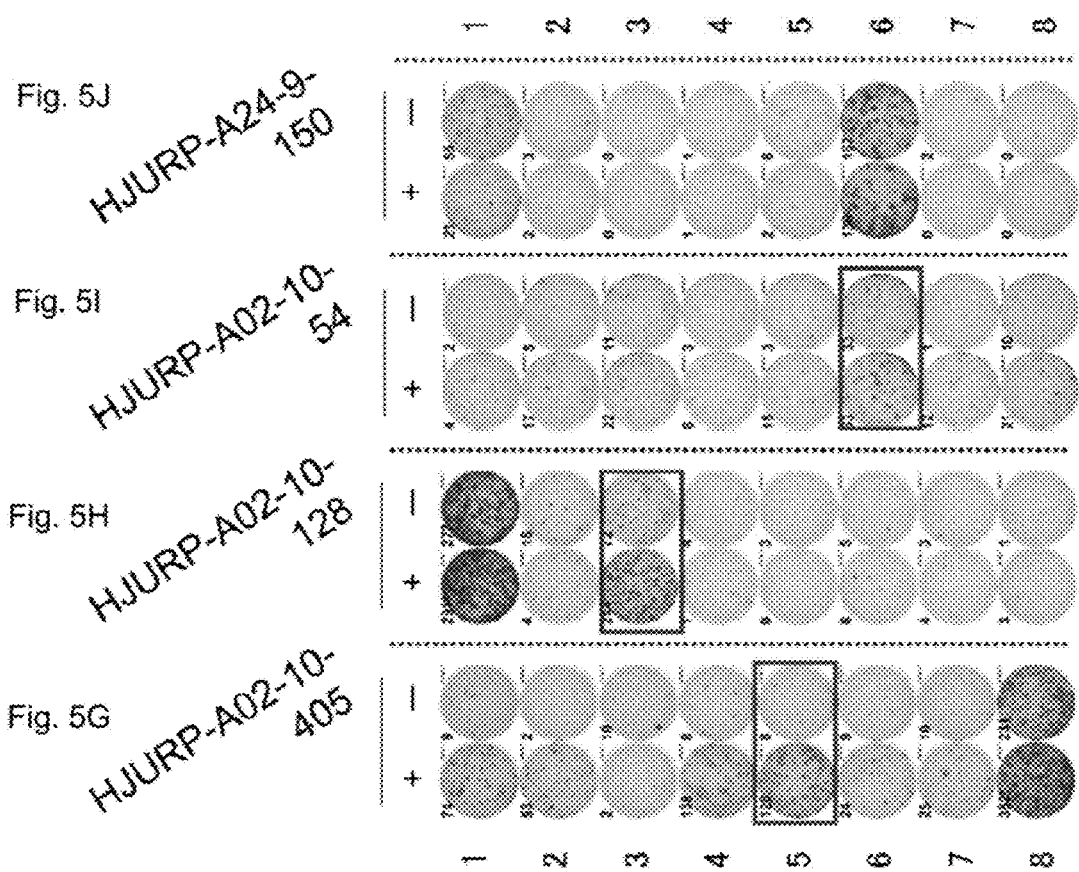

HJURP-A02-9-406 #4-175

HJURP-A02-9-129 #5-108

HJURP-A02-10-405 #5-115

HJURP-A02-10-128 #3-65

HJURP PEPTIDES AND VACCINES INCLUDING THE SAME

CROSS REFERENCE TO RELATED APPLICATIONS

This application is a divisional application of U.S. application Ser. No. 14/205,163, filed Mar. 11, 2014, which is a divisional application of U.S. application Ser. No. 13/583,195, filed Nov. 15, 2012, now U.S. Pat. No. 8,933,014, issued Jan. 13, 2015, which is the U.S. National Phase of PCT/JP2011/001407, filed Mar. 10, 2011, which claims the benefit of U.S. Provisional Applications No. 61/312,931, filed on Mar. 11, 2010, and 61/315,320, filed on Mar. 18, 2010 the contents of which are hereby incorporated herein by reference in their entirety.

TECHNICAL FIELD

The present invention relates to the field of biological science, more specifically to the field of cancer therapy. In particular, the present invention relates to novel peptides that are extremely effective as cancer vaccines as well as drugs for treating and preventing tumors.

REFERENCE TO SEQUENCE LISTING

This application includes a Sequence Listing as a text file named "87331-1016381-SEQULIST.txt" created Jun. 29, 2016, and containing 22,654 bytes. The material contained in this text file is incorporated by reference in its entirety for all purposes.

BACKGROUND ART

It has been demonstrated that CD8 positive CTLs recognize epitope peptides derived from tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered through immunological approaches (NPL 1, Boon T, Int J Cancer 1993 May 8, 54(2): 177-80; NPL 2, Boon T & van der Bruggen P, J Exp Med 1996 Mar. 1, 183(3): 725-9). Some of these TAAs are currently undergoing clinical development as immunotherapeutic targets.

Favorable TAAs are indispensable for the proliferation and survival of cancer cells. The use of such TAAs as targets for immunotherapy may minimize the well-described risk of immune escape of cancer cells attributable to deletion, mutation, or down-regulation of TAAs as a consequence of therapeutically driven immune selection. Accordingly, the identification of new TAAs, capable of inducing potent and specific anti-tumor immune responses warrants further development of clinical investigation of peptide vaccination strategies for various types of cancer is ongoing (NPL 3, Harris C C, J Natl Cancer Inst 1996 Oct. 16, 88(20): 1442-55; NPL 4, Butterfield L H et al., Cancer Res 1999 Jul. 1, 59(13): 3134-42; NPL 5, Vissers J L et al., Cancer Res 1999 Nov. 1, 59(21): 5554-9; NPL 6, van der Burg S H et al., J Immunol 1996 May 1, 156(9): 3308-14; NPL 7, Tanaka F et al., Cancer Res 1997 Oct. 15, 57(20): 4465-8; NPL 8, Fujie T et al., Int J Cancer 1999 Jan. 18, 80(2): 169-72; NPL 9, Kikuchi M et al., Int J Cancer 1999 May 5, 81(3): 459-66; NPL 10, Oiso M et al., Int J Cancer 1999 May 5, 81(3): 387-94). To date, several clinical trials using these tumor-associated antigen derived peptides have been reported. Unfortunately, many of the current cancer vaccine trial have shown only a low objective response rate (NPL 11, Belli F et al., J Clin Oncol 2002 Oct. 15, 20(20): 4169-80; NPL 12, Coulie P G et al., Immunol Rev 2002 Oct. 188: 33-42; NPL 13, Rosenberg S A et al., Nat Med 2004 Sep. 10(9): 909-15). Accordingly, there remains a need for new TAAs as immunotherapeutic targets.

HJURP (reference sequence is shown in GenBank Accession No: NM_018410), Holliday junction recognizing protein, was identified from genome-wide expression profile analysis of non-small cell lung cancer using cDNA microarray composed of 27,648 genes (NPL 14, Kato T et al., Cancer Res. 2007 Sep. 15; 67(18):8544-53). HJURP is involved in the homologous recombination pathway in the DSB (DNA double-strand break) repair process through interaction with hMSH5 (human MutS homologue 5) and NBS1 (Nijmegen breakage syndrome protein 1), which is a part of the MRN protein complex. Treatment of cancer cells with small interfering RNA (siRNA) against HJURP caused abnormal chromosomal fusions and led to genomic instability and senescence. In addition, HJURP overexpression was observed in a majority of human lung cancers (PTL 1, WO2004/031413). Taken together, these data suggests that HJURP may be applicable to the target of cancer immunotherapy for patient.

CITATION LIST

Patent Literature

[PTL 1] WO2004/031413

Non Patent Literature

[NPL 1] Boon T, Int J Cancer 1993 May 8, 54(2): 177-80
[NPL 2] Boon T & van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8
[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Kato T et al., Cancer Res. 2007 Sep. 15; 67(18):8544-53

SUMMARY OF INVENTION

The present invention is based, at least in part, on the discovery of the suitable targets of immunotherapy. Because TAAs are generally perceived by the immune system as "self" and therefore often have no immunogenicity, the discovery of appropriate targets is of extreme importance. Recognizing that HJURP (SEQ ID NO: 50), typically encoded by the gene of GenBank Accession No. NM_018410 (SEQ ID NO: 49) has been identified as up-regulated in cancers, including, but not limited to, acute myeloid leukemia (AML), bladder cancer, breast cancer, cervical cancer, cholangiocellular carcinoma, chronic myeloid leukemia (CML), colorectal cancer, esophagus cancer, Diffused-type gastric cancer, liver cancer, non-small cell lung cancer (NSCLC), lymphoma, osteosarcoma, ovarian cancer, pancreatic cancer, prostate cancer, renal carcinoma, small cell lung cancer (SCLC), soft tissue tumor and testicular tumor, the present invention focuses on HJURP as a candidate for the target of cancer/tumor immunotherapy, more particularly novel HJURP epitope peptides that may serve as suitable immunotherapeutic targets.

To that end, the present invention is directed, at least in part, to the identification of specific epitope peptides among the gene products of HJURP that possess the ability to induce CTLs specific to HJURP. As discussed in detail below, peripheral blood mononuclear cells (PBMCs) obtained from a healthy donor were stimulated using HLA-A*2402 or HLA-A*0201 binding candidate peptides derived from HJURP. CTL lines were then established with specific cytotoxicity against the HLA-A24- or HLA-A2-positive target cells pulsed with each of candidate peptides. The results herein demonstrate that these peptides are HLA-A24 or HLA-A2 restricted epitope peptides that may induce potent and specific immune responses against cells expressing HJURP. These results further demonstrate that HJURP is strongly immunogenic and that the epitopes thereof are effective targets for cancer/tumor immunotherapy.

Accordingly, it is an object of the present invention to provide isolated peptides binding to HLA antigen, derived from HJURP (SEQ ID NO: 50) and the immunologically active fragments thereof. Such peptides are expected to have CTL inducibility and, thus, can be used to induce CTL ex vivo or to be administered to a subject for inducing immune responses against cancers examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor. Preferred peptides are nonapeptides or decapeptides, and more preferably, a nonapeptide or decapeptide having an amino acid sequence selected from among SEQ ID NOs: 2 to 24 and 26 to 48. Peptides having an amino acid sequence selected from among SEQ ID NOs: 3, 4, 7, 18, 23, 26, 27, 30, 31, 32, 35, 37, 38 and 43 showed strong CTL inducibility and thus are particularly preferred.

The present invention also contemplates modified peptides having an amino acid sequence selected from among SEQ ID NOs: 2 to 24 and 26 to 48, wherein one, two or more amino acids are substituted deleted or added, so long as the modified peptides retain the requisite original CTL inducibility.

The present invention further encompasses isolated polynucleotides encoding any peptides of the present invention. These polynucleotides can be used to induce or prepare APCs with CTL inducibility or, like the above-described peptides of the present invention, can be administered to a subject for inducing immune responses against cancers.

When administered to a subject, the present peptides are presented on the surface of APCs so as to induce CTLs targeting the respective peptides. Therefore, one object of the present invention is to provide agents, compositions or substances that include or incorporate any peptides or polynucleotides of the present invention for inducing CTLs. Such agents, compositions and/or substances can be used for the treatment and/or prophylaxis and/or postoperative recurrence of cancers, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor. Thus, it is yet another object of the present invention to provide pharmaceutical agents, compositions or substances for the treatment and/or prophylaxis and/or prevention of postoperative recurrence of cancer that include or incorporate any peptides or polynucleotides of the present invention. Instead of or in addition to the present peptides or polynucleotides, the pharmaceutical agents, compositions or substances of the present invention may include as active ingredients APCs or exosomes that present any of the present peptides.

The peptides or polynucleotides of the present invention may be used to induce APCs that present on the surface a complex of an HLA antigen and a present peptide, for example, by contacting APCs derived from a subject with the peptide or introducing a polynucleotide encoding a peptide of the present invention into APCs. Such APCs have high CTL inducibility against target peptides and find use in cancer immunotherapy. Accordingly, the present invention encompasses the methods for inducing APCs with CTL inducibility as well as APCs obtained by such methods.

It is a further object of the present invention to provide a method for inducing CTL, such methods including the step of co-culturing CD8 positive cells with APCs or exosomes presenting the peptide of the present invention on its surface or the step of introducing a gene that includes a polynucleotide encoding a T cell receptor (TCR) subunit polypeptide binding to the present peptide. CTLs obtained by such methods find use in the treatment and/or prevention of cancers, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor. Therefore, it is yet another object of present invention to provide CTLs obtained by the present methods.

It is yet another object of the present invention to provide methods for inducing an immune response against cancer in a subject in need thereof, such methods including the step of administering compositions or substances including the HJURP polypeptides or immunologically active fragments thereof, polynucleotides encoding HJURP polypeptides, exosomes or the APCs presenting HJURP polypeptides.

The applicability of the present invention extends to any of a number of diseases relating to or arising from HJURP overexpression, such as cancer, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

More specifically, the present invention provides followings:

[1] An isolated peptide consisting of the amino acid sequence of SEQ ID NO: 50 or an immunologically active fragment thereof, wherein said peptide binds an HLA antigen and has cytotoxic T lymphocyte (CTL) inducibility,

[2] The isolated peptide of [1], wherein the HLA antigen is HLA-A24,

[3] The isolated peptide of [1], wherein the HLA antigen is HLA-A2,

[4] The isolated peptide of [1] or [2], wherein said peptide comprises an amino acid sequence selected from the group consisting of SEQ ID NOs: 2 to 24,

[5] The isolated peptide of [1] or [3], wherein said peptide comprises an amino acid sequence selected from the group consisting of SEQ ID NOs: 26 to 48,

[6] An isolated peptide selected from the group consisting of:
(a) an isolated peptide that binds to an HLA antigen, has cytotoxic T lymphocytes (CTL) inducibility, and consists of the amino acid sequence of SEQ ID NO: 50 or an immunologically active fragment thereof,
(b) the isolated peptide of (a), wherein the HLA antigen is HLA-A24,
(c) the isolated peptide of (a) or (b), which comprises an amino acid sequence selected from the group consisting of SEQ ID NOs: 2 to 24, and
(d) the isolated peptide of (a) or (b), wherein said peptide comprises a modified peptide having of an amino acid sequence selected from the group consisting of SEQ ID NOs: 2 to 24, wherein 1, 2, or several amino acid(s) are substituted, deleted, or added, provided said modified peptide retains the CTL inducibility of the original peptide,

[7] An isolated peptide selected from the group consisting of:
(a) an isolated peptide binding to an HLA antigen and having cytotoxic T lymphocytes (CTL) inducibility, wherein the peptide consists of the amino acid sequence of SEQ ID NO: 50 or an immunologically active fragment thereof,
(b) the isolated peptide of (a), wherein the HLA antigen is HLA-A2,
(c) the isolated peptide of (a) or (b), which comprises an amino acid sequence selected from the group consisting of SEQ ID NOs: 26 to 48, and
(d) the isolated peptide of (a) or (b), wherein said peptide comprises a modified peptide having an amino acid sequence selected from the group consisting of SEQ ID NOs: 26 to 48, wherein 1, 2, or several amino acid(s) are substituted, deleted, or added provided said modified peptide retains the CTL inducibility of the original peptide,

[8] The isolated peptide of [6] which consists of an amino acid sequence selected from the group consisting of SEQ ID NOs: 2 to 24, wherein the peptide has one or both of the following characteristics:
(a) The second amino acid from N-terminus is selected from the group consisting of phenylalanine, tyrosine, methionine and tryptophan; and
(b) The C-terminal amino acid is selected from the group consisting of phenylalanine, leucine, isoleucine, tryptophan and methionine,

[9] The isolated peptide of [7], which consists of an amino acid sequence selected from the group consisting of SEQ ID NOs: 26 to 48, wherein the peptide has one or both of the following characteristics:
(a) The second amino acid from the N-terminus is selected from the group consisting of phenylalanine, tyrosine, methionine and tryptophan; and
(b) The C-terminal amino acid is selected from the group consisting of phenylalanine, leucine, isoleucine, tryptophan and methionine,

[10] The isolated peptide of any one of [1] to [9], wherein said peptide is nonapeptide or decapeptide,

[11] An isolated polynucleotide encoding the peptide of any one of [1] to [10],

[12] A composition for inducing CTL, wherein the composition comprises one or more peptide(s) of any one of [1] to [10], or one or more polynucleotide(s) of [11],

[13] A pharmaceutical composition for the treatment and/or prophylaxis of cancers, and/or the prevention of a postoperative recurrence thereof, wherein the composition comprises one or more peptide(s) of any one of [1] to [10], or one or more polynucleotides of [11],

[14] The pharmaceutical composition of [13], wherein said composition is formulated for the administration to a subject whose HLA antigen is HLA-A24,

[15] The pharmaceutical composition of [13], wherein said composition is formulated for the administration to a subject whose HLA antigen is HLA-A2,

[16] The pharmaceutical composition of [13] to [15], wherein said composition is formulated for the treatment of cancer,

[17] A method for inducing an antigen-presenting cell (APC) with CTL inducibility comprising a step selected from the group consisting of:
(a) contacting an APC with a peptide of any one of [1] to [10] in vitro, ex vivo or in vivo, and
(b) introducing a polynucleotide encoding the peptide of any one of [1] to [10] into an APC,

[18] A method for inducing CTL by a method that comprises a step selected from the group consisting of:
(a) co-culturing CD8 positive T cells with APCs that present on the surface a complex of an HLA antigen and the peptide of any one of [1] to [10];
(b) co-culturing CD8 positive T cells with exosomes that presents on the surface a complex of an HLA antigen and a peptide of any one of [1] to [10]; and
(c) introducing a gene that comprises a polynucleotide encoding a T cell receptor (TCR) subunit polypeptide bound to a peptide of any one of [1] to [10] into a T cell,

[19] An isolated APC that presents on its surface a complex of an HLA antigen and the peptide of any one of [1] to [10],

[20] The APC of [19], which is induced by the method of [17],

[21] An isolated CTL that targets any of the peptides of [1] to [10],

[22] A CTL of [21] induced by the method of [18],

[23] A method of inducing an immune response against cancer in a subject in need thereof, said method comprising the step of administering to the subject a composition comprising a peptide of [1] to [10], an immunologically active fragment thereof, or a polynucleotide encoding the peptide or the fragment,

[24] An antibody or immunologically active fragment thereof against any of the peptides of [1] to [10],

[25] A vector comprising a nucleotide sequence encoding any of the peptides of [1] to [10],

[26] A diagnostic kit comprising any of the peptides of [1] to [10], the nucleotide of [1] or the antibody of [24],

[27] The isolated peptide of any one of [1], [2], [4], [6], [8], and [10], wherein the peptide consists of the amino acid sequence selected from the group consisting of SEQ ID NOs: 3, 4, 7, 18 and 23,

[28] The isolated peptide of any one of [1], [3], [5], [7], [9], and [10], wherein the peptide consists of the amino acid sequence selected from the group consisting of SEQ ID NOs: 26, 27, 30, 31, 32, 35, 37, 38 and 43,

[29] An exosome that presents a complex comprising any of the peptides of [1] to [10] and an HLA antigen, and

[30] A host cell transformed or transfected with an expression vector according to [25].

It is to be understood that both the foregoing summary of the present invention and the following detailed description are of exemplified embodiments, and not restrictive of the present invention or other alternate embodiments of the present invention.

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIGS. 1A-1F is composed of a series of photographs depicting the results of IFN-gamma ELISPOT assays on CTLs that were induced with peptides derived from HJURP. The CTLs in well number #4 stimulated with HJURP-A24-9-28 (SEQ ID NO: 3) (FIG. 1A), in #4 with HJURP-A24-9-263 (SEQ ID NO: 4) (FIG. 1B), in #4 with HJURP-A24-9-408 (SEQ ID NO: 7) (FIG. 1C), in #6 with HJURP-A24-10-383 (SEQ ID NO: 18) (FIG. 1D) and in #4 with HJURP-A24-10-162 (SEQ ID NO: 23) (FIG. 1E), showed potent IFN-gamma production compared with the control, respectively. The square on the well of these pictures indicates that the cells from corresponding well were expanded to establish CTL lines. In contrast, as is the typical case for negative data, no specific IFN-gamma production was detected from the CTL stimulated with HJURP-A24-9-149 (SEQ ID NO: 1) against peptide-pulsed target cells (FIG. 1F). The square on the well of these pictures indicated that the cells from corresponding well were expanded to establish CTL lines. In the figures, "+" indicates the IFN-gamma production against target cells pulsed with the appropriate peptide, and "−" indicates the IFN-gamma production against target cells not pulsed with any peptides.

FIGS. 5A-5J is composed of a series of photographs depicting the results of IFN-gamma ELISPOT assays on CTLs that were induced with peptides derived from HJURP. The CTLs in well number #4 stimulated with HJURP-A02-9-496 (SEQ ID NO: 26) (FIG. 5A), in #2 with HJURP-A02-9-354 (SEQ ID NO: 27) (FIG. 5B), in #4 with HJURP-A02-9-406 (SEQ ID NO: 30) (FIG. 5C), in #5 with HJURP-A02-9-129 (SEQ ID NO: 31) (FIG. 5D), in #3 with HJURP-A02-9-599 (SEQ ID NO:32) (FIG. 5E), and in #1 with HJURP-A02-9-386 (SEQ ID NO: 35) (FIG. 5F) showed potent IFN-gamma production compared with the control, respectively. The square on the well of these pictures indicates that the cells from corresponding well were expanded to establish CTL lines. In contrast, as is the typical case with negative data, no specific IFN-gamma production was detected from the CTL stimulated with HJURP-A02-9-150 (SEQ ID NO: 25) (FIG. 5J). In the figures, "+" indicates the IFN-gamma production against target cells pulsed with the appropriate peptide, and "−" indicates the IFN-gamma production against target cells not pulsed with any peptides.

FIGS. 5G-5J is composed of a series of photographs depicting the results of IFN-gamma ELISPOT assays on CTLs that were induced with peptides derived from HJURP. The CTLs in #5 with HJURP-A02-10-405 (SEQ ID NO: 37) (FIG. 5G), in #3 with HJURP-A02-10-128 (SEQ ID NO: 38) (FIG. 5H) and in #6 with HJURP-A02-10-54 (SEQ ID NO: 43) (FIG. 5I) showed potent IFN-gamma production compared with the control, respectively. The square on the well of these pictures indicates that the cells from corresponding well were expanded to establish CTL lines. In contrast, as is the typical case with negative data, no specific IFN-gamma production was detected from the CTL stimulated with HJURP-A02-9-150 (SEQ ID NO: 25) (FIG. 5J). In the figures, "+" indicates the IFN-gamma production against target cells pulsed with the appropriate peptide, and "−" indicates the IFN-gamma production against target cells not pulsed with any peptides.

DESCRIPTION OF EMBODIMENTS

Figure 2A:
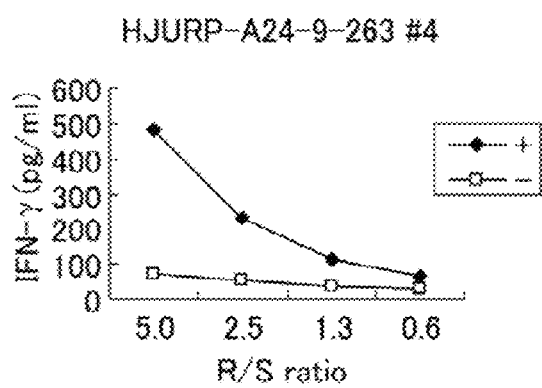
FIGS. 2A-2B is composed of a series of line graphs depicting the results of an IFN-gamma ELISA assay that, in turn, demonstrates the IFN-gamma production of CTL lines stimulated with HJURP-A24-9-263 (SEQ ID NO: 4) (FIG. 2A) and HJURP-A24-9-408 (SEQ ID NO: 7) (FIG. 2B). The results demonstrate that CTL lines established by stimulation with each peptide show potent IFN-gamma production as compared with the control. In the figures, "+" indicates the IFN-gamma production against target cells pulsed with the appropriate peptide and "−" indicates the IFN-gamma production against target cells not pulsed with any peptides.
Figure 2B:
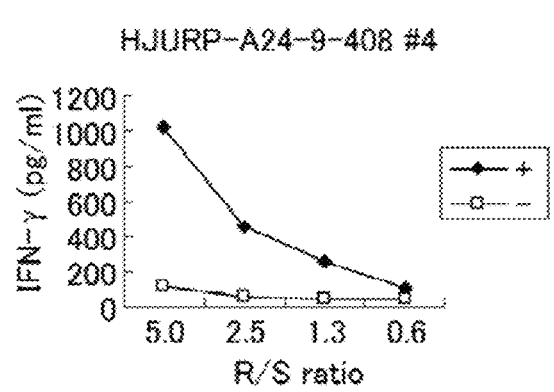

Although any methods and materials similar or equivalent to those described herein can be used in the practice or testing of embodiments of the present invention, the preferred materials, methods, and devices are now described. However, before the present materials and methods are described, it should be understood that these descriptions are merely illustrative only and not intended to be limiting. It should also be understood that the present invention is not limited to the particular sizes, shapes, dimensions, materials, methodologies, protocols, etc. described herein, as these may vary in accordance with routine experimentation and/or optimization. Furthermore, the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

Unless otherwise defined, all technical and scientific terms used herein have the same meaning as commonly understood by one of ordinary skill in the art to which the present invention belongs. In case of conflict, the present specification, including definitions, will control. In addition, the materials, methods, and examples are illustrative only and not intended to be limiting.

I. Definitions

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue(s) may be modified residue(s), or non-naturally occurring residue(s), such as artificial chemical mimetic(s) of corresponding naturally occurring amino acid(s), as well as to naturally occurring amino acid polymers.

The term "oligopeptide" sometimes used in the present specification is used to refer to peptides of the present invention which are 20 residues or fewer, typically 15 residues or fewer in length and is typically composed of between about 8 and about 11 residues, often 9 or 10 residues The term "amino acid" as used herein refers to naturally occurring and synthetic amino acids, as well as amino acid analogs and amino acid mimetics that similarly function to the naturally occurring amino acids. Amino acid may be either L-amino acids or D-amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have one or more modified R group(s) or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein and, unless otherwise specifically indicated are similarly to the amino acids referred to by their commonly accepted single-letter codes.

The terms "agent", "substance" and "composition" are used interchangeably herein to refer to a product that includes the specified ingredients in the specified amounts, as well as any product that results, directly or indirectly, from combination of the specified ingredients in the specified amounts. Such terms in relation to the modifier "pharmaceutical" are intended to encompass a product that includes the active ingredient(s), and any inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, in the context of the present invention, the terms "pharmaceutical agent" and "pharmaceutical composition" are used interchangeably to refer to any agent, substance or composition made by admixing a product of the present invention and a pharmaceutically or physiologically acceptable carrier.

The phrase "pharmaceutically acceptable carrier" or "physiologically acceptable carrier", as used herein, means a pharmaceutically or physiologically acceptable material, composition, substance or vehicle, including but not limited to, a liquid or solid filler, diluent, excipient, solvent or encapsulating material, involved in carrying or transporting the subject scaffolded polypharmacophores from one organ, or portion of the body, to another organ, or portion of the body.

The pharmaceutical agents or compositions of the present invention find particular use as vaccines. In the context of the present invention, the phrase "vaccine" (also referred to as an "immunogenic composition") refers to a substance that has the function to induce anti-tumor immunity upon inoculation into animals.

Unless otherwise defined, the term "cancer" refers to the cancers overexpressing HJURP gene, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

Unless otherwise defined, the terms "cytotoxic T lymphocyte", "cytotoxic T cell" and "CTL" are used interchangeably herein and unless otherwise specifically indicated, refer to a sub-group of T lymphocytes that are capable of recognizing non-self cells (e.g., tumor/cancer cells, virus-infected cells) and inducing the death of such cells.

Unless otherwise defined, the terms "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, the term "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

As used herein, in the context of a subject or patient, the phrase "HLA-A2 positive" refers to that the subject or patient homozygously or heterozygously possess HLA-A2 antigen gene, and HLA-A2 antigen is expressed in cells of the subject or patient as an HLA antigen.

Similarly, as used herein, in the context of a subject or patient, the phrase "HLA-A24 positive" also refers to that the subject or patient homozygously or heterozygously possess HLA-A24 antigen gene, and HLA-A24 antigen is expressed in cells of the subject or patient as an HLA antigen.

To the extent that the methods and compositions of the present invention find utility in the context of the "treatment" of cancer, a treatment is deemed "efficacious" if it leads to clinical benefit such as, reduction in expression of HJURP gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the materials and methods of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis can include a wide range of prophylactic therapies aimed at alleviating the severity of the particular disorder, e.g. reducing the proliferation and metastasis of tumors.

In the context of the present invention, the treatment and/or prophylaxis of cancer and/or the prevention of postoperative recurrence thereof include any of the following steps, such as the surgical removal of cancer cells, the inhibition of the growth of cancerous cells, the involution or regression of a tumor, the induction of remission and suppression of occurrence of cancer, the tumor regression, and the reduction or inhibition of metastasis. Effective treatment and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multi specific antibodies (e.g. bispecific antibodies) formed from at least two intact antibodies, and antibody fragments so long as they exhibit the desired biological activity. An "antibody" indicates all classes (e.g. IgA, IgD, IgE, IgG and IgM).

Unless otherwise defined, all technical and scientific terms used herein have the same meaning as commonly understood by one of ordinary skill in the art to which the present invention belongs.

II. Peptides

To demonstrate that peptides derived from HJURP function as an antigen recognized by CTLs, peptides derived from HJURP (SEQ ID NO: 50) were analyzed to determine whether they were antigen epitopes restricted by HLA-A24 or A2 which are commonly encountered HLA alleles (Date Y et al., Tissue Antigens 47: 93-101, 1996; Kondo A et al., J Immunol 155: 4307-12, 1995; Kubo R T et al., J Immunol 152: 3913-24, 1994).

Candidates of HLA-A24 binding peptides derived from HJURP were identified using the information on their binding affinities to HLA-A24. The following candidate peptide were identified"

HJURP-A24-9-576 (SEQ ID NO: 2),
HJURP-A24-9-28 (SEQ ID NO: 3),
HJURP-A24-9-263 (SEQ ID NO: 4),
HJURP-A24-9-403 (SEQ ID NO: 5),
HJURP-A24-9-388 (SEQ ID NO: 6),
HJURP-A24-9-408 (SEQ ID NO: 7),
HJURP-A24-9-544 (SEQ ID NO: 8),
HJURP-A24-9-280 (SEQ ID NO: 9),
HJURP-A24-10-149 (SEQ ID NO: 10),
HJURP-A24-10-395 (SEQ ID NO: 11),
HJURP-A24-10-729 (SEQ ID NO: 12),
HJURP-A24-10-56 (SEQ ID NO: 13),
HJURP-A24-10-590 (SEQ ID NO: 14),
HJURP-A24-10-635 (SEQ ID NO: 15),
HJURP-A24-10-389 (SEQ ID NO: 16),
HJURP-A24-10-28 (SEQ ID NO: 17),
HJURP-A24-10-383 (SEQ ID NO: 18),
HJURP-A24-10-379 (SEQ ID NO: 19),
HJURP-A24-10-235 (SEQ ID NO: 20),
HJURP-A24-10-218 (SEQ ID NO: 21),
HJURP-A24-10-388 (SEQ ID NO: 22),
HJURP-A24-10-162 (SEQ ID NO: 23), and
HJURP-A24-10-627 (SEQ ID NO: 24).

Moreover, after in vitro stimulation of T-cells by dendritic cells (DCs) pulsed (loaded) with these peptides, CTLs were successfully established by stimulating the DCs with each of the following peptides:

HJURP-A24-9-28 (SEQ ID NO: 3),
HJURP-A24-9-263 (SEQ ID NO: 4),
HJURP-A24-9-408 (SEQ ID NO: 7),
HJURP-A24-10-383 (SEQ ID NO: 18), and
HJURP-A24-10-162 (SEQ ID NO: 23).

These established CTLs showed potent specific CTL activity against target cells pulsed with respective peptides. These results demonstrate that HJURP is an antigen recognized by CTLs and that the peptides tested are epitope peptides of HJURP restricted by HLA-A24.

Candidates of HLA-A2 binding peptides derived from HJURP were identified based on their binding affinities to HLA-A2. The following candidate peptides were identified:

HJURP-A2-9-496 (SEQ ID NO: 26),
HJURP-A2-9-354 (SEQ ID NO: 27),
HJURP-A2-9-266 (SEQ ID NO: 28),
HJURP-A2-9-51 (SEQ ID NO: 29),
HJURP-A2-9-406 (SEQ ID NO: 30),
HJURP-A2-9-129 (SEQ ID NO: 31),
HJURP-A2-9-599 (SEQ ID NO: 32),
HJURP-A2-9-226 (SEQ ID NO: 33),
HJURP-A2-9-274 (SEQ ID NO: 34),
HJURP-A2-9-386 (SEQ ID NO: 35),
HJURP-A2-9-244 (SEQ ID NO: 36),
HJURP-A2-10-405 (SEQ ID NO: 37),
HJURP-A2-10-128 (SEQ ID NO: 38),
HJURP-A2-10-649 (SEQ ID NO: 39),
HJURP-A2-10-273 (SEQ ID NO: 40),
HJURP-A2-10-266 (SEQ ID NO: 41),
HJURP-A2-10-598 (SEQ ID NO: 42),
HJURP-A2-10-54 (SEQ ID NO: 43),
HJURP-A2-10-731 (SEQ ID NO: 44),
HJURP-A2-10-397 (SEQ ID NO: 45),
HJURP-A2-10-157 (SEQ ID NO: 46),
HJURP-A2-10-455 (SEQ ID NO: 47) and
HJURP-A2-10-156 (SEQ ID NO: 48).

Moreover, after in vitro stimulation of T-cells by dendritic cells (DCs) pulsed (loaded) with these peptides, CTLs were successfully established using each of the following peptides;

HJURP-A2-9-496 (SEQ ID NO: 26),
HJURP-A2-9-354 (SEQ ID NO: 27),
HJURP-A2-9-406 (SEQ ID NO: 30),
HJURP-A2-9-129 (SEQ ID NO: 31),
HJURP-A2-9-599 (SEQ ID NO: 32),
HJURP-A2-9-386 (SEQ ID NO: 35),
HJURP-A2-10-405 (SEQ ID NO: 37),
HJURP-A2-10-128 (SEQ ID NO: 38), and
HJURP-A2-10-54 (SEQ ID NO: 43).

These established CTLs showed potent specific CTL activity against target cells pulsed with respective peptides. These results demonstrate that HJURP is an antigen recognized by CTLs and that the peptides tested are epitope peptides of HJURP restricted by HLA-A2.

Since the HJURP gene is over expressed in cancer cells such as AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor and not expressed in most normal organs, it is a good target for cancer immunotherapy. Thus, the present invention provides nonapeptides (peptides composed of nine amino acid residues) and decapeptides (peptides composed of ten amino acid residues) of CTL-recognized epitopes from HJURP. Alternatively, the present invention provides isolated peptides which bind to HLA antigens and induce cytotoxic T lymphocytes (CTLs), wherein the peptide has an amino acid sequence selected from among of SEQ ID NO: 50 or is an immunologically active fragment thereof. More specifically, in some embodiments, the present invention provides peptides having an amino acid sequence selected from among SEQ ID NOs: 2 to 24 and 26 to 48.

Generally, software programs now available, for example, on the Internet, such as those described in Parker K C et al., J Immunol 1994 Jan. 1, 152(1): 163-75 and Nielsen M et al., Protein Sci 2003; 12: 1007-17 can be used to calculate the binding affinities between various peptides and HLA antigens in silico. Binding affinity with HLA antigens can be measured as described, for example, in Parker K C et al., J Immunol 1994 Jan. 1, 152(1): 163-75, Kuzushima K et al., Blood 2001, 98(6): 1872-81, Larsen M V et al. BMC Bioinformatics. 2007 Oct. 31; 8: 424, Buus S et al. Tissue Antigens., 62:378-84, 2003, Nielsen M et al., Protein Sci 2003; 12: 007-17, and Nielsen M et al. PLoS ONE 2007; 2: e796, which are summarized in, e.g., Lafuente E M et al., Current Pharmaceutical Design, 2009, 15, 3209-3220. Methods for determining binding affinity are described, for example, in the Journal of Immunological Methods (1995, 185: 181-190) and Protein Science (2000, 9: 1838-1846). Therefore, one can use such software programs to select those fragments derived from HJURP that have high binding affinity with HLA antigens. Accordingly, the present invention encompasses peptides composed of any fragments derived from HJURP, which would be determined to bind with HLA antigens by such known programs. Furthermore, such peptides may include the peptide composed of the full length of HJURP.

The peptides of the present invention, particularly the nonapeptides and decapeptides of the present invention, may be flanked with additional amino acid residues so long as the peptides retain their CTL inducibility. The particular additional amino acid residues may be composed of any kind of amino acids so long as they do not impair the CTL inducibility of the original peptide. Thus, the present invention encompasses peptides having a binding affinity for HLA antigens, including peptides derived from HJURP. Such peptides are, for example, less than about 40 amino acids, often less than about 20 amino acids, usually less than about 15 amino acids.

Generally, it is known that modifications of one or more amino acids in a peptide do not influence the function of the peptide, or in some cases even enhance the desired function of the original protein. In fact, modified peptides (i.e., peptides composed of an amino acid sequence modified by substituting, deleting, inserting, or adding one, two or several amino acid residues to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, according to one embodiment of the present invention, the peptide having CTL inducibility of the present invention may be composed of a peptide having an amino acid sequence selected from among SEQ ID NOs: 2 to 24 and 26 to 48, wherein one, two or even more amino acids are added, deleted and/or substituted.

Those of skill in the art will recognize that individual additions, deletions, insertions, or substitutions to an amino acid sequence that alters a single amino acid or a small percentage of amino acids results in the conservation of the properties of the original amino acid side-chain; it is thus referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic group containing side-chain (H, F, Y, W). In addition, the following eight groups each contain amino acids that are conservative substitutions for one another:
1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be peptides of the present invention. However, the peptide of the present invention is not restricted thereto and may include non-conservative modifications, so long as the resulting modified peptide retains the CTL inducibility of the original peptide. Furthermore, the modified peptides should not exclude CTL inducible peptides of polymorphic variants, interspecies homologues, and alleles of HJURP.

Amino acid residues may be inserted, substituted or added to the peptides of the present invention or, alternatively, amino acid residues may be deleted there from to achieve a higher binding affinity. To retain the requisite CTL inducibility, one preferably modifies (inserts, deletes, adds and/or substitutes) only a small number (for example, 1, 2 or several) or a small percentage of amino acids. Herein, the term "several" means 5 or fewer amino acids, for example, 4 or 3 or fewer. The percentage of amino acids to be modified may be 20% or less, for example, 15% or less, even more preferably 10% or less, for example 1 to 5%.

When used in cancer immunotherapy, the present peptides are presented on the surface of a cell or exosome as a complex with an HLA antigen. Therefore, it is preferable to select peptides that not only induce CTLs but also possess high binding affinity to the HLA antigen. To that end, the peptides can be modified by substitution, insertion, and/or addition of the amino acid residues to yield a modified peptide having improved binding affinity. In addition to peptides that are naturally displayed, since the regularity of the sequences of peptides displayed by binding to HLA antigens has already been known (J Immunol 1994, 152: 3913; Immunogenetics 1995, 41: 178; J Immunol 1994, 155: 4307), modifications based on such regularity may be introduced into the immunogenic peptides of the present invention.

For example, peptides possessing high HLA-A24 binding affinity tend to have the second amino acid from the N-terminus substituted with phenylalanine, tyrosine, methionine, or tryptophan. Likewise, peptides in which the C-terminal amino acid is substituted with phenylalanine, leucine, isoleucine, tryptophan, or methionine can also be favorably used. Thus, peptides having an amino acid sequence selected from among SEQ ID NOs: 2 to 24 wherein the second amino acid from the N-terminus of the amino acid sequence of the SEQ ID NO is substituted with phenylalanine, tyrosine, methionine, or tryptophan, and peptides, and/or wherein the C-terminus of the amino acid sequence of the SEQ ID NO is substituted with phenylalanine, leucine, isoleucine, tryptophan, or methionine are encompassed by the present invention.

Alternatively, in, peptides showing high HLA-A2 binding affinity, it may be desirable to substitute the second amino acid from the N-terminus with leucine or methionine or the amino acid at the C-terminus with valine or leucine. Thus, peptides having amino acid sequences selected from among SEQ ID NOs: 26 to 48 wherein the second amino acid from the N-terminus of the amino acid sequence of the SEQ ID NO is substituted with leucine or methionine, and peptides, and/or wherein the C-terminus of the amino acid sequence of the SEQ ID NO is substituted with valine or leucine are encompassed by the present invention.

Substitutions may be introduced not only at the terminal amino acids but also at the position of potential T cell receptor (TCR) recognition of peptides. Several studies have demonstrated that a peptide with amino acid substitutions may have equal to or better function than that of the original, for example, CAP1, p53$_{(264-272)}$, Her-2/neu$_{(369-377)}$ or gp100$_{(209-217)}$ (Zaremba et al. Cancer Res. 57, 4570-4577, 1997, T. K. Hoffmann et al. J Immunol. (2002) Feb. 1; 168(3):1338-47., S. O. Dionne et al. Cancer Immunol immunother. (2003) 52: 199-206 and S. O. Dionne et al. Cancer Immunology, Immunotherapy (2004) 53, 307-314).

The present invention also contemplates the addition of one, two or several amino acids to the N and/or C-terminus of the present peptides. Such modified peptides having high HLA antigen binding affinity and retained CTL inducibility are also included in the present invention. For example, the present invention provides an isolated peptide of less than 14, 13, 12, 11, or 10 amino acids in length comprising the amino acid sequence selected from the group consisting of:

(i) an amino acid sequence selected from the group consisting of SEQ ID NOs: 2 to 9, and 26 to 36, wherein 1, 2, or several amino acid(s) are substituted, wherein the peptide binds an HLA antigen and induces cytotoxic T lymphocytes, and (ii) the amino acid sequence of (i), wherein the amino acid sequence has one or both of the following characteristics:

(a) the second amino acid from the N-terminus of said SEQ ID NO is selected from the group consisting of leucine or methionine; and (b) the C-terminal amino acid of said SEQ ID NO is selected from the group consisting of valine or leucine.

Moreover, the present invention also provides an isolated peptide of less than 15, 14, 13, 12, or 11 amino acids in length comprising the amino acid sequence selected from the group consisting of:

(i') an amino acid sequence selected from the group consisting of SEQ ID NOs: 10 to 24, and 37 to 48, wherein 1, 2, or several amino acid(s) are substituted, wherein the peptide binds an HLA antigen and induces cytotoxic T lymphocytes, and (ii') the amino acid sequence of (i'), wherein the amino acid sequence has one or both of the following characteristics:

(a) the second amino acid from the N-terminus of said SEQ ID NO is selected from the group consisting of leucine or methionine; and (b) the C-terminal amino acid of said SEQ ID NO is selected from the group consisting of valine or leucine.

These peptides are processed in APC to present a peptide of (i), (ii), (i'), and (ii') thereon, when these peptides are contacted with, or introduced in APC.

However, when the peptide sequence is identical to a portion of the amino acid sequence of an endogenous or exogenous protein having a different function, side effects such as autoimmune disorders or allergic symptoms against specific substances may be induced. Therefore, one can perform homology searches using available databases to avoid situations in which the sequence of the peptide matches the amino acid sequence of another protein. When it becomes clear from the homology searches that there exists not even a peptide with 1 or 2 amino acids difference to the objective peptide, the objective peptide may be modified in order to increase its binding affinity with HLA antigens, and/or increase its CTL inducibility without any danger of such side effects.

Although peptides having high binding affinity to the HLA antigens as described above are expected to be highly effective, the candidate peptides, which are selected according to the presence of high binding affinity as an indicator, are further examined for the presence of CTL inducibility. Herein, the phrase "CTL inducibility" indicates the ability of the peptide to induce CTLs when presented on antigen-presenting cells (APCs). Further, "CTL inducibility" includes the ability of the peptide to induce CTL activation, CTL proliferation, promote CTL lysis of target cells, and to increase CTL IFN-gamma production.

Confirmation of CTL inducibility is accomplished by inducing APCs carrying human MHC antigens (for example, B-lymphocytes, macrophages, and dendritic cells (DCs)), or more specifically DCs derived from human peripheral blood mononuclear leukocytes, and after stimulation with the peptides, mixing with CD8 positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 2000 August, 61(8): 764-79, Related Articles, Books, Linkout Induction of CTL response by a minimal epitope vaccine in HLA A*0201/DR1 transgenic mice: dependent on MHC (HLA) class II restricted T(H) response) can be used. For example, the target cells may be radiolabeled with 51Cr and such, and cytotoxic activity may be calculated from radioactivity released from the target cells. Alternatively, it may be examined by measuring IFN-gamma produced and released by CTL in the presence of APCs that carry immobilized peptides, and visualizing the inhibition zone on the media using anti-IFN-gamma monoclonal antibodies.

As a result of examining the CTL inducibility of the peptides as described above, it was discovered that nona-peptides or decapeptides selected from among those peptides having an amino acid sequence indicated by SEQ ID NOs: 2 to 24 and 26 to 48 showed particularly high CTL inducibility as well as high binding affinity to an HLA antigen. Thus, these peptides are exemplified as preferred embodiments of the present invention.

Furthermore, homology analysis results demonstrated that such peptides do not have significant homology with peptides derived from any other known human gene products. This lowers the possibility of unknown or undesired immune responses arising when used for immunotherapy. Therefore, also from this aspect, these peptides are useful for eliciting immunity against HJURP in cancer patients. Thus, the peptides of the present invention, preferably, peptides having an amino acid sequence selected from among SEQ ID NOs: 2 to 24 and 26 to 48.

In addition to modification of the present peptides, discussed above, the peptides of the present invention may be linked to other peptides, so long as the resulting linked peptide retains the requisite CTL inducibility of the original peptide and, more preferably, also retain the requisite HLA binding. Exemplary "other" peptides include: the peptides of the present invention or the CTL inducible peptides derived from other TAAs. The linkers between the peptides are well known in the art, for example, AAY (P. M. Daftarian et al., J Trans Med 2007, 5:26), AAA, NKRK (R. P. M. Sutmuller et al., J Immunol. 2000, 165: 7308-7315) or K (S. Ota et al., Can Res. 62, 1471-1476, K. S. Kawamura et al., J Immunol. 2002, 168: 5709-5715).

For example, non-HJURP tumor associated antigen peptides also can be used substantially simultaneously to increase immune response via HLA class I and/or class II. It is well established that cancer cells can express more than one tumor associated gene. It is within the scope of routine experimentation for one of ordinary skill in the art to determine whether a particular subject expresses additional tumor associated genes, and then to include HLA class I and/or HLA class II binding peptides derived from expression products of such genes in HJURP compositions or vaccines according to the present invention.

Examples of HLA class I and HLA class II binding peptides will be known to one of ordinary skill in the art (for example, see Coulie, Stem Cells 13:393-403, 1995), and can be used in the invention in a like manner as those disclosed herein. One of ordinary skill in the art can prepare polypeptides including one or more HJURP peptides and one or more of the non-HJURP peptides, or nucleic acids encoding such polypeptides, according to standard procedures of molecular biology.

The above-linked peptides are referred to herein as "polytopes", i.e., groups of two or more potentially immunogenic or immune response stimulating peptides which can be joined together in various arrangements (e.g., concatenated, overlapping). The polytope (or nucleic acid encoding the polytope) can be administered in a standard immunization protocol, e.g., to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., Proc. Natl. Acad. Sci USA 92(13):5845-5849, 1995; Gilbert et al., Nature Biotechnol. 15(12):1280-1284, 1997; Thomson et al., J Immunol. 157(2):822-826, 1996; Tarn et al., J Exp. Med. 171(0:299-306, 1990). Polytopes containing various numbers and combinations of epitopes can be prepared and tested for recognition by CTLs and for efficacy in increasing an immune response.

Furthermore, the peptides of the present invention may be further linked to other substances, so long as they retain the CTL inducibility. Such substances may include: peptides, lipids, sugar and sugar chains, acetyl groups, natural and synthetic polymers, etc. The peptides may contain modifications such as glycosylation, side chain oxidation, or phosphorylation; so long as the modifications do not destroy the biological activity of the peptides as described herein. These kinds of modifications may be performed to confer additional functions (e.g., targeting function, and delivery function) or to stabilize the polypeptide.

For example, to increase the in vivo stability of a polypeptide, it is known in the art to introduce D-amino acids, amino acid mimetics or unnatural amino acids; this concept may also be adopted for the present polypeptides. The stability of a polypeptide may be assayed in a number of ways. For instance, peptidases and various biological media, such as human plasma and serum, can be used to test stability (see, e.g., Verhoef et al., Eur J Drug Metab Pharmacokin 1986, 11: 291-302).

Moreover, as noted above, among the modified peptides that are substituted, deleted or added by one, two or several amino acid residues, those having same or higher activity as compared to original peptides can be screened for or selected. The present invention, therefore, also provides the method of screening for or selecting modified peptides having same or higher activity as compared to originals. For example, the method may include steps of:

a: substituting, deleting or adding at least one amino acid residue of a peptide of the present invention, b: determining the activity of the peptide, and c: selecting the peptide having same or higher activity as compared to the original.

Herein, the activity may include MHC binding activity, APC or CTL inducibility and cytotoxic activity.

Herein, the peptides of the present invention may also be described as "HJURP peptide(s)" or "HJURP polypeptide(s)".

III. Preparation Of Hjurp Peptides

The peptides of the present invention may be prepared using well known techniques. For example, the peptides may be prepared synthetically, by recombinant DNA technology or chemical synthesis. The peptides of the present invention may be synthesized individually or as longer polypeptides including two or more peptides. The peptides may be isolated, i.e., purified or isolated substantially free from other naturally occurring host cell proteins and fragments thereof, or any other chemical substances.

The peptides of the present invention may contain modifications, such as glycosylation, side chain oxidation, or phosphorylation; provided such modifications do not destroy the biological activity of the original peptides. Other illustrative modifications include incorporation of D-amino acids or other amino acid mimetics that may be used, for example, to increase the serum half life of the peptides.

A peptide of the present invention may be obtained through chemical synthesis based on the selected amino acid sequence. For example, conventional peptide synthesis methods that may be adopted for the synthesis include:

(i) Peptide Synthesis, Interscience, New York, 1966;

(ii) The Proteins, Vol. 2, Academic Press, New York, 1976;

(iii) Peptide Synthesis (in Japanese), Maruzen Co., 1975;

(iv) Basics and Experiment of Peptide Synthesis (in Japanese), Maruzen Co., 1985;

(v) Development of Pharmaceuticals (second volume) (in Japanese), Vol. 14 (peptide synthesis), Hirokawa, 1991;

(vi) WO99/67288; and (vii) Barany G. & Merrifield R. B., Peptides Vol. 2, "Solid Phase Peptide Synthesis", Academic Press, New York, 1980, 100-118.

Alternatively, the present peptides may be obtained adopting any known genetic engineering methods for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. Such vectors and host cells are also provided by the present invention. The host cell is then cultured to produce the peptide of interest. The peptide may also be produced in vitro adopting an in vitro translation system.

IV. Polynucleotides

The present invention provides polynucleotides which encode any of the aforementioned peptides of the present invention. These include polynucleotides derived from the natural occurring HJURP gene (GenBank Accession No. NM_018410 (for example, SEQ ID NO: 49)) and those having a conservatively modified nucleotide sequences thereof. Herein, the phrase "conservatively modified nucleotide sequence" refers to sequences which encode identical or essentially identical amino acid sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon may be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill in the art will recognize that each codon in a nucleic acid (except AUG, which is ordinarily the only codon for methionine, and TGG, which is ordinarily the only codon for tryptophan) may be modified to yield a functionally identical molecule.

Accordingly, each silent variation of a nucleic acid that encodes a peptide is implicitly described in each disclosed sequence.

The polynucleotide of the present invention may be composed of DNA, RNA, and derivatives thereof. As is well known in the art, a DNA molecule is suitably composed of bases such as the naturally occurring bases A, T, C, and G, and T is replaced by U in an RNA. One of skill will recognize that non-naturally occurring bases be included in polynucleotides, as well.

The polynucleotide of the present invention may encode multiple peptides of the present invention with or without intervening amino acid sequences. For example, the intervening amino acid sequence may provide a cleavage site (e.g., enzyme recognition sequence) of the polynucleotide or the translated peptides. Furthermore, the polynucleotide may include any additional sequences to the coding sequence encoding the peptide of the present invention. For example, the polynucleotide may be a recombinant polynucleotide that includes regulatory sequences required for the expression of the peptide or may be an expression vector (plasmid) with marker genes and such. In general, such recombinant polynucleotides may be prepared by the manipulation of polynucleotides through conventional recombinant techniques using, for example, polymerases and end nucleases.

Both recombinant and chemical synthesis techniques may be used to produce the polynucleotides of the present invention. For example, a polynucleotide may be produced by insertion into an appropriate vector, which may be expressed when transfected into a competent cell. Alternatively, a polynucleotide may be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide may be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles called exosomes, which present complexes formed between the peptides of the present invention and HLA antigens on their surface. Exosomes may be prepared, for example, using the methods detailed in Japanese Patent Application Kohyo Publications No. Hei 11-510507 and WO99/03499, and may be prepared using APCs obtained from patients who are subject to treatment and/or prevention. The exosomes of the present invention may be inoculated as vaccines, similarly to the peptides of the present invention.

The type of HLA antigens included in the complexes must match that of the subject requiring treatment and/or prevention. For example, in the Japanese population, HLA-A24 or HLA-A2, particularly HLA-A*2402 and HLA-A*0201 and HLA-A*0206 are often appropriate. The use of A24 type or the A2 type that is highly expressed among the Japanese and Caucasian is favorable for obtaining effective results, and subtypes such as A*0201 and A*0206 find use. Typically, in the clinic, the type of HLA antigen of the patient requiring treatment is investigated in advance, which enables appropriate selection of peptides having high levels of binding affinity to this antigen, or having CTL inducibility by antigen presentation. Furthermore, in order to obtain peptides showing high binding affinity and CTL inducibility, substitution, deletion, or addition of 1, 2, or several amino acids may be performed based on the amino acid sequence of the naturally occurring HJURP partial peptide.

When using the A24 type HLA antigen for the exosome of the present invention, peptides having a sequence of any one of SEQ ID NOs: 2 to 24 have particular utility. Alternatively, when using the A2 type HLA antigen for the exosome of the present invention, the peptides having a sequence of any one of SEQ ID NOs: 26 to 48 find use.

VI. Antigen-Presenting Cells (APCs)

The present invention also provides isolated APCs that present complexes formed with HLA antigens and the peptides of the present invention on its surface. The APCs may be derived from patients who are subject to treatment and/or prevention, and may be administered as vaccines by themselves or in combination with other drugs including the peptides of the present invention, exosomes, or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since DC is a representative APC having the strongest CTL inducing activity among APCs, DCs find use as the APCs of the present invention.

For example, the APCs of the present invention may be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention are induced in the body of the subject. Therefore, the APCs of the present invention may be obtained by collecting the APCs from the subject after administering the peptides of the present invention to the subject. Alternatively, the APCs of the present invention may be obtained by contacting APCs collected from a subject with the peptide of the present invention.

The APCs of the present invention may be administered to a subject for inducing immune response against cancer in the subject by themselves or in combination with other drugs including the peptides, exosomes or CTLs of the present invention. For example, the ex vivo administration may include steps of:

a: collecting APCs from a first subject,
b: contacting with the APCs of step a, with the peptide, and
c: administering the APCs of step b to a second subject.

The first subject and the second subject may be the same individual, or may be different individuals. The APCs obtained by step b may be administered as a vaccine for treating and/or preventing cancer, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor, but not limited thereto.

The present invention also provides a method or process for manufacturing a pharmaceutical composition for inducing APCs, wherein the method includes the step of admixing or formulating the peptide of the invention with a pharmaceutically acceptable carrier.

According to an aspect of the present invention, the APCs have a high level of CTL inducibility. In the term of "high level of CTL inducibility", the high level is relative to the level of that by APC contacting with no peptide or peptides which may not induce the CTL. Such APCs having a high level of CTL inducibility may be prepared by a method which includes the step of transferring a polynucleotide encoding the peptide of the present invention to APCs in vitro as well as the method mentioned above. The introduced genes may be in the form of DNAs or RNAs. Examples of methods for introduction include, without particular limitations, various methods conventionally performed in this field, such as lipofection, electroporation, or calcium phosphate method may be used. More specifically, it may be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MEW Class I or Class II, and proceeds through a presentation pathway to present partial peptides.

VII. Cytotoxic T Lymphocytes (CTLs)

A CTL induced against any of the peptides of the present invention strengthens the immune response targeting cancer cells in vivo and thus may be used as vaccines similar to the peptides. Thus, the present invention provides isolated CTLs that are specifically induced or activated by any of the present peptides.

Such CTLs may be obtained by (1) administering the peptide(s) of the present invention to a subject or (2) contacting (stimulating) subject-derived APCs, and CD8 positive cells, or peripheral blood mononuclear leukocytes in vitro with the peptide(s) of the present invention or (3) contacting CD8 positive cells or peripheral blood mononuclear leukocytes in vitro with the APCs or exosomes presenting a complex of an HLA antigen and the peptide on its surface or (4) introducing a gene that includes a polynucleotide encoding a T cell receptor (TCR) subunit binding to the peptide of the present invention. Such APCs or exosomes may be prepared by the methods described above and details of the method of (4) is described bellow in section "VIII. T cell receptor (TCR)".

The CTLs of the present invention may be derived from patients who are subject to treatment and/or prevention, and may be administered by themselves or in combination with other drugs including the peptides of the present invention or exosomes for the purpose of regulating effects. The obtained CTLs act specifically against target cells presenting the peptides of the present invention, for example, the same peptides used for induction. The target cells may be cells that endogenously express HJURP, such as cancer cells, or cells that are transfected with the HJURP gene; and cells that present a peptide of the present invention on the cell surface due to stimulation by the peptide may also serve as targets of activated CTL attack.

VIII. T Cell Receptor (TCR)

The present invention also provides a composition including nucleic acids encoding polypeptides that are capable of forming a subunit of a T cell receptor (TCR), and methods of using the same. The TCR subunits have the ability to form TCRs that confer specificity to T cells against tumor cells presenting HJURP. By using the known methods in the art, the nucleic acids of alpha- and beta-chains as the TCR subunits of the CTL induced with one or more peptides of the present invention may be identified (WO2007/032255 and Morgan et al., J Immunol, 171, 3288 (2003)). For example, the PCR method is preferred to analyze the TCR. The PCR primers for the analysis can be, for example, 5'-R primers (5'-gtctaccaggcattcgcttcat-3') as 5' side primers (SEQ ID NO: 51) and 3-TRa-C primers (5'-tcagctggaccaca-gccgcagcgt-3') specific to TCR alpha chain C region (SEQ ID NO: 52), 3-TRb-C1 primers (5'-tcagaaatcctttctcttgac-3') specific to TCR beta chain C1 region (SEQ ID NO: 53) or 3-TRbeta-C2 primers (5'-ctagcctctggaatcctttctctt-3') specific to TCR beta chain C2 region (SEQ ID NO: 54) as 3' side primers, but not limited thereto. The derivative TCRs may bind target cells displaying the HJURP peptide with high avidity, and optionally mediate efficient killing of target cells presenting the HJURP peptide in vivo and in vitro.

The nucleic acids encoding the TCR subunits may be incorporated into suitable vectors, e.g., retroviral vectors. These vectors are well known in the art. The nucleic acids or the vectors including them usefully may be transferred into a T cell, for example, a T cell from a patient. Advantageously, the present invention provides an off-the-shelf composition allowing rapid modification of a patient's own T cells (or those of another mammal) to rapidly and easily produce modified T cells having excellent cancer cell killing properties.

The specific TCR is a receptor capable of specifically recognizing a complex of a peptide of the present invention and HLA molecule, giving a T cell specific activity against the target cell when the TCR is presented on the surface of the T cell. A specific recognition of the above complex may be confirmed by any known methods, and preferred methods include, for example, HLA multimer staining analysis using HLA molecules and peptides of the present invention, and ELISPOT assay. By performing the ELISPOT assay, it can be confirmed that a T cell expressing the TCR on the cell surface recognizes a cell by the TCR, and that the signal is transmitted intracellularly. The confirmation that the above-mentioned complex can give a T cell cytotoxic activity when the complex exists on the T cell surface may also be carried out by a known method. A preferred method includes, for example, the determination of cytotoxic activity against an HLA positive target cell, such as chromium release assay.

Also, the present invention provides CTLs which are prepared by transduction with the nucleic acids encoding the TCR subunits polypeptides that bind to the HJURP peptide of, e.g., SEQ ID NOs: 2 to 24 in the context of HLA-A24, and also the peptides of SEQ ID NOs: 26 to 48 in the context of HLA-A2.

The transduced CTLs are capable of homing to cancer cells in vivo, and may be expanded by well known culturing methods in vitro (e.g., Kawakami et al., J Immunol., 142, 3452-3461 (1989)). The CTLs of the present invention may be used to form an immunogenic composition useful in treating or the prevention of cancer in a patient in need of therapy or protection (WO2006/031221).

IX. Pharmaceutical Substances Or Compositions

Since HJURP expression is specifically elevated in cancer such as AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor compared with normal tissue, the peptides of or polynucleotides of the present invention may be used for the treatment and/or for the prophylaxis of cancer, and/or prevention of postoperative recurrence thereof. Thus, the present invention provides a pharmaceutical agent, substance or composition for the treatment and/or prophylaxis of cancer, and/or for prevention of postoperative recurrence thereof, such agent, substance or composition including as an active ingredient one or more of the peptides, or polynucleotides of the present invention as an active ingredient. Alternatively, the present peptides may be expressed on the surface of any of the foregoing exosomes or cells, such as APCs for the use as pharmaceutical substances or compositions. In addition, the aforementioned CTLs which target any of the peptides of the present invention may also be used as the active ingredient of the present pharmaceutical substances or compositions.

In the present invention, the phrase "active ingredient" refers to a substance in an agent or composition that is biologically or physiologically active. Particularly, in a pharmaceutical agent or composition, "active ingredient" refers to a substance that shows an objective pharmacological effect. For example, in case of pharmaceutical agents or compositions for use in the treatment or prevention of cancer, active ingredients in the agents or compositions may lead to at least one biological or physiologically action on cancer cells and/or tissues directly or indirectly. Preferably, such action may include reducing or inhibiting cancer cell growth, damaging or killing cancer cells and/or tissues, and so on. Before formulated, "active ingredient" is also referred to as "bulk", "drug substance" or "technical product".

The present pharmaceutical agents or compositions find use as a vaccine. In the present invention, the phrase "vaccine" (also referred to as an immunogenic composition) refers to a substance that has the function to induce antitumor immunity upon inoculation into animals.

The pharmaceutical agents or compositions of the present invention can be used for the treatment and/or prevention cancers, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

In another embodiment, the present invention also provides the use of an active ingredient in manufacturing a pharmaceutical composition or agent for treating cancer or tumor, said active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

Alternatively, the present invention further provides an active ingredient for use in treating or preventing cancer of tumor, said active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

Alternatively, the present invention further provides a method or process for manufacturing a pharmaceutical composition or substance for treating or preventing cancer or tumor, wherein the method or process includes the step of formulating a pharmaceutically or physiologically acceptable carrier with an active ingredient selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

In another embodiment, the present invention also provides a method or process for manufacturing a pharmaceutical composition or substance for treating or preventing cancer or tumor, wherein the method or process includes the steps of admixing an active ingredient with a pharmaceutically or physiologically acceptable carrier, wherein the active ingredient is selected from among:
 (a) a peptide of the present invention;
 (b) a nucleic acid encoding such a peptide as disclosed herein in an expressible form;
 (c) an APC or an exosome presenting a peptide of the present invention on its surface; and
 (d) a cytotoxic T cell of the present invention.

The pharmaceutical agents, substances or compositions of the present invention can be used to treat and/or prevent cancers or tumors, and/or prevention of postoperative recurrence thereof in subjects or patients including human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, peptides having an amino acid sequence selected from among SEQ ID NOs: 2 to 24 have been found to be HLA-A24 restricted epitope peptides or the candidates and also SEQ ID NOs: 26 to 48 have been found to be HLA-A2 restricted epitope peptides or the candidates that may induce potent and specific immune response. Therefore, the present pharmaceutical substances or compositions which include any of these peptides with the amino acid sequences of SEQ ID NOs: 2 to 24 and 26 to 48 are particularly suited for the administration to subjects whose HLA antigen is HLA-A24 or HLA-A2. The same applies to pharmaceutical substances or compositions which include polynucleotides encoding any of these peptides (i.e., the polynucleotides of the present invention).

Cancers to be treated by the pharmaceutical substances or compositions of the present invention are not limited and include any cancer in which HJURP is involved (e.g., is overexpressed), including, but not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present pharmaceutical substances or compositions may contain in addition to the aforementioned active ingredients, other peptides which have the ability to induce CTLs against cancerous cells, other polynucleotides encoding the other peptides, other cells that present the other peptides, or such. Herein, the other peptides that have the ability to induce CTLs against cancerous cells are exemplified by cancer specific antigens (e.g., identified TAAs), but are not limited thereto.

If needed, the pharmaceutical substances or compositions of the present invention may optionally include other therapeutic substances as an active ingredient, so long as the substance does not inhibit the antitumoral effect of the active ingredient, e.g., any of the present peptides. For example, formulations may include anti-inflammatory substances or compositions, pain killers, chemotherapeutics, and the like. In addition to other therapeutic substances in the medicament itself, the medicaments of the present invention may also be administered sequentially or concurrently with the one or more other pharmacologic substances or compositions. The amounts of medicament and pharmacologic substance or composition depend, for example, on what type of pharmacologic substance(s) or composition(s) is/are used, the disease being treated, and the scheduling and routes of administration.

It should be understood that in addition to the ingredients particularly mentioned herein, the pharmaceutical substances or compositions of the present invention may include other substances or compositions conventional in the art having regard to the type of formulation in question.

In one embodiment of the present invention, the present pharmaceutical agents, substances or compositions may be included in articles of manufacture and kits containing materials useful for treating the pathological conditions of the disease to be treated, e.g., cancer. The article of manufacture may include a container of any of the present pharmaceutical substances or compositions with a label. Suitable containers include bottles, vials, and test tubes. The containers may be formed from a variety of materials, such as glass or plastic. The label on the container should indicate the substance or composition is used for treating or prevention of one or more conditions of the disease. The label may also indicate directions for administration and so on.

In addition to the container described above, a kit including a pharmaceutical agent, substance or composition of the present invention may optionally further include a second container housing a pharmaceutically-acceptable diluent. It may further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Substances or Compositions Containing the Peptides as the Active Ingredient The peptides of the present invention can be administered directly as a pharmaceutical agent, substance or composition, or if necessary, may be formulated by conventional formulation methods. In the latter case, in addition to the peptides of the present invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical substances or compositions can contain as necessary, stabilizers, suspensions, preservatives, surfactants and such. The pharmaceutical agent, substances or compositions of the present invention can be used for anticancer purposes.

The peptides of the present invention can be prepared in combination, which includes two or more of peptides of the present invention, to induce CTL in vivo. The peptides can be in a cocktail or can be conjugated to each other using standard techniques. For example, the peptides can be chemically linked or expressed as a single fusion polypeptide sequence that may have one or several amino acid(s) as a linker (e.g., Lysine linker: K. S. Kawamura et al. J. Immunol. 2002, 168: 5709-5715). The peptides in the combination can be the same or different. By administering the peptides of the present invention, the peptides are presented in high density by the HLA antigens on APCs, then CTLs that specifically react toward the complex formed between the displayed peptide and the HLA antigen are induced. Alternatively, APCs (e.g., DCs) are removed from subjects and then stimulated by the peptides of the present invention to obtain APCs that present any of the peptides of the present invention on their cell surface. These APCs are re-administered to the subjects to induce CTLs in the subjects, and as a result, aggressiveness towards the tumor-associated endothelium can be increased.

The pharmaceutical substances or compositions for the treatment and/or prevention of cancer, which include any of the peptides of the present invention as the active ingredient, can include an adjuvant so that cellular immunity will be established effectively, or they can be administered with other active ingredients, and they can be administered by formulation into granules. An adjuvant refers to any compound, substance or composition that enhances the immune response against the protein when administered together (or successively) with the protein having immunological activity. An adjuvant that can be applied includes those described in the literature (Clin Microbiol Rev 1994, 7: 277-89). Exemplary adjuvants include aluminum phosphate, aluminum hydroxide, alum, cholera toxin, salmonella toxin, Incomplete Freund's adjuvant (IFA), Complete Freund's adjuvant (CFA), ISCOMatrix, GM-CSF, CpG, O/W emulsion, and such, but are not limited thereto.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Preferable examples of the salts include salts with an alkali metal, salts with a metal, salts with an organic base, salts with an organic acid and salts with an inorganic acid. As used herein, "pharmaceutically acceptable salt" refers to those salts which retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like. Examples of preferred salts include salts with an alkali metal, salts with a metal, salts with an organic base, salts with an organic acid and salts with an inorganic acid.

In some embodiments, the pharmaceutical agents, substances or compositions of the present invention include a component that primes CTL. Lipids have been identified as substances or compositions capable of priming CTL in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTL when covalently attached to an appropriate peptide (see, e.g., Deres et al., Nature 1989, 342: 561-4).

The method of administration can be oral, intradermal, subcutaneous, intravenous injection, or such, and systemic administration or local administration to the vicinity of the targeted sites. The administration can be performed by single administration or boosted by multiple administrations. The dose of the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once in a few days to few months. One skilled in the art can appropriately select a suitable dose.

(2) Pharmaceutical Substances or Compositions Containing Polynucleotides as Active Ingredient The pharmaceutical substances or compositions of the present invention can also include nucleic acids encoding the peptide(s) disclosed herein in an expressible form. Herein, the phrase "in an expressible form" means that the polynucleotide, when introduced into a cell, will be expressed in vivo as a polypeptide that induces anti-tumor immunity. In an exemplified embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors. See also, e.g., Wolff et al., Science 1990, 247: 1465-8; U.S. Pat. Nos. 5,580,859; 5,589,466; 5,804,566; 5,739,118; 5,736,524; 5,679,647; and WO 98/04720). Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, Salmonella typhi vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a patient can be either direct, in which case the patient is directly exposed to a polynucleotide-carrying vector, or indirect, in which case, cells are first transformed with the polynucleotide of interest in vitro, then the cells are transplanted into the patient. Theses two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology that are applicable to the present invention are described by Ausubel et al., in Current Protocols in Molecular Biology, John Wiley & Sons, N Y, 1993; and by Krieger, in Gene Transfer and Expression, A Laboratory Manual, Stockton Press, N Y, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1,000 mg, for example, 0.01 mg to 100 mg, for example, 0.1 mg to 10 mg, and can be administered once every a few days to once every few months. One skilled in the art can appropriately select the suitable dose.

X. Methods Using the Peptides, Exosomes, Apcs and Ctls

The peptides and polynucleotides of the present invention can be used for preparing or inducing APCs and CTLs. The exosomes and APCs of the present invention can be also used for inducing CTLs. The peptides, polynucleotides, exosomes and APCs can be used in combination with any other compounds so long as the additional compounds do not inhibit CTL inducibility. Thus, any of the aforementioned pharmaceutical substances or compositions of the present invention can be used for inducing CTLs. In addition thereto, those including the peptides and polynucleotides can be also be used for inducing APCs as explained below.

(1) Method of Inducing Antigen-Presenting Cells (APCs)

The present invention provides methods of inducing APCs with high CTL inducibility using the peptides or polynucleotides of the present invention.

The methods of the present invention include the step of contacting APCs with the peptides of the present invention in vitro, ex vivo or in vivo. For example, the method contacting APCs with the peptides ex vivo can include steps of:

a: collecting APCs from a subject, and
b: contacting the APCs of step a with the peptide.

The APCs are not limited to a particular kind of cells and include DCs, Langerhans cells, macrophages, B cells, and activated T cells, which are known to present proteinaceous antigens on their cell surface so as to be recognized by lymphocytes. Preferably, DCs can be used since they have the strongest CTL inducibility among APCs. Any peptides of the present invention can be used by themselves or with other peptides of the present invention.

On the other hands, when the peptides of the present invention are administered to a subject, the APCs are contacted with the peptides in vivo, consequently, the APCs with high CTL inducibility are induced in the body of the subject. Thus, the present invention includes administering the peptides of the present invention to a subject. Similarly, when the polynucleotides of the present invention are administered to a subject in an expressible form, the peptides of the present invention are expressed and contacted with APCs in vivo, consequently, the APCs with high CTL inducibility are induced in the body of the subject. Thus, the present invention may also include administering the polynucleotides of the present invention to a subject. "Expressible form" is described above in section "IX. Pharmaceutical substances or compositions, (2) Pharmaceutical substances or compositions containing polynucleotides as the active ingredient".

Furthermore, the present invention may include introducing the polynucleotide of the present invention into an APCs to induce APCs with CTL inducibility. For example, the method can include steps of:

a: collecting APCs from a subject, and
b: introducing a polynucleotide encoding peptide of the present invention.

Step b can be performed as described above in section "VI. Antigen-presenting cells".

Alternatively, the present invention provides a method for preparing an antigen-presenting cell (APC) which specifically induces CTL activity against HJURP, wherein the method can include one of the following steps:

(a) contacting an APC with a peptide of the present invention in vitro, ex vivo or in vivo; and
(b) introducing a polynucleotide encoding a peptide of the present invention into an APC.

(2) Method of Inducing CTLs

The present invention also provides methods for inducing CTLs using the peptides, polynucleotides, exosomes or APCs of the present invention.

The present invention also provides methods for inducing CTLs using a polynucleotide encoding a polypeptide that is capable of forming a T cell receptor (TCR) subunit recognizing a complex of the peptides of the present invention and HLA antigens. Preferably, the methods for inducing CTLs may include at least one step selected from among:

a) contacting a CD8 positive T cell with an antigen-presenting cell and/or an exosome that presents on its surface a complex of an HLA antigen and a peptide of the preset invention; and b) introducing a polynucleotide encoding a polypeptide that is capable of forming a TCR subunit recognizing a complex of a peptide of the present invention and an HLA antigen into a CD8 positive cell.

When the peptides, the polynucleotides, APCs, or exosomes of the present invention are administered to a subject, CTLs are induced in the body of the subject, and the strength of the immune response targeting the cancer cells is enhanced. Thus, the methods of the present invention includes the step of administering the peptides, the polynucleotides, the APCs or exosomes of the present invention to a subject.

Alternatively, CTLs can be also induced by using them ex vivo, and after inducing CTL, the activated CTLs can be returned to the subject. For example, the method can include steps of:

a: collecting APCs from a subject;

b: contacting with the APCs of step a, with the peptide; and c: co-culturing the APCs of step b with CD8 positive cells.

The APCs to be co-cultured with the CD8 positive cells in above step c can also be prepared by transferring a gene that includes a polynucleotide of the present invention into APCs as described above in section "VI. Antigen-presenting cells"; though the present invention is limited thereto, and encompasses any APCs that effectively present on its surface a complex of an HLA antigen and a peptide of the present invention.

Instead of such APCs, the exosomes that presents on the surface a complex of an HLA antigen and the peptide of the present invention can be also used. Namely, the present invention can include the step of co-culturing exosomes presenting on its surface a complex of an HLA antigen and the peptide of the present invention. Such exosomes can be prepared by the methods described above in section "V. Exosomes".

Furthermore, CTL can be induced by introducing a gene that includes a polynucleotide encoding the TCR subunit binding to the peptide of the present invention into CD8 positive cells. Such transduction can be performed as described above in section "VIII. T cell receptor (TCR)".

In addition, the present invention provides a method or process for manufacturing a pharmaceutical agent, substance or composition inducing CTLs, wherein the method includes the step of admixing or formulating the peptide of the present invention with a pharmaceutically acceptable carrier.

(3) Method of Inducing Immune Response

Moreover, the present invention provides methods of inducing an immune response against diseases related to HJURP. Suitable diseases may include cancer, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

The methods of the present invention may include the step of administering substance(s) or composition(s) containing any of the peptides of the present invention or polynucleotides encoding them. The present inventive method may also contemplate the administration of exosomes or APCs presenting any of the peptides of the present invention. For details, see the item of "IX. Pharmaceutical substances or compositions", particularly the part describing the use of the pharmaceutical substances or compositions of the present invention as vaccines. In addition, the exosomes and APCs that can be employed for the present methods for inducing immune response are described in detail under the items of "V. Exosomes", "VI. Antigen-presenting cells (APCs)", and (1) and (2) of "X. Methods using the peptides, exosomes, APCs and CTLs", supra.

The present invention also provides a method or process for manufacturing a pharmaceutical agent, substance or composition inducing immune response, wherein the method may include the step of admixing or formulating the peptide of the present invention with a pharmaceutically acceptable carrier.

Alternatively, the method of the present invention may include the step of administrating a vaccine or a pharmaceutical composition of the present invention that contains:

(a) a peptide of the present invention;

(b) a nucleic acid encoding such a peptide as disclosed herein in an expressible form;

(c) an APC or an exosome presenting a peptide of the present invention on its surface; or (d) a cytotoxic T cell of the present invention.

In the context of the present invention, a cancer overexpressing HJURP can be treated with these active ingredients. Examples of such cancers include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor. Accordingly, prior to the administration of the vaccines or pharmaceutical compositions including the active ingredients, it is preferable to confirm whether the expression level of HJURP in the biological samples to be treated is enhanced compared with normal cells of the same organ. Thus, in one embodiment, the present invention provides a method for treating cancer (over)expressing HJURP, which method may include the steps of:

i) determining the expression level of HJURP in biological sample (s) obtained from a subject with the cancer to be treated;

ii) comparing the expression level of HJURP with normal control; and iii) administrating at least one component selected from among (a) to (d) described above to a subject with cancer overexpressing HJURP compared with normal control.

Alternatively, the present invention also provides a vaccine or pharmaceutical composition that includes at least one component selected from among (a) to (d) described above, for use in administrating to a subject having cancer overexpressing HJURP. In other words, the present invention further provides a method for identifying a subject to be treated with the HJURP polypeptide of the present invention, such methods including the step of determining an expression level of HJURP in subject-derived biological sample (s), wherein an increase of the level compared to a normal control level of the gene indicates that the subject may have cancer which may be treated with the HJURP polypeptide of the present invention. The methods of treating cancer of the present invention are described in more detail below.

Any subject-derived cell or tissue can be used for the determination of HJURP expression so long as it includes the objective transcription or translation product of HJURP. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of HJURP in biological samples obtained from a subject may be determined. The expression level can be determined at the transcription (nucleic acid) product level, using methods known in the art. For example, the mRNA of HJURP may be quantified using probes by hybridization methods (e.g., Northern hybridization). The detection may be carried out on a chip, an array or as such. The use of an array may be preferable for detecting the expression level of HJURP. Those skilled in the art can prepare such probes utilizing the sequence information of HJURP. For example, the cDNA of HJURP may be used as the probes. If necessary, the probes may be labeled with a suitable label, such as dyes, fluorescent substances and isotopes, and the expression level of the gene may be detected as the intensity of the hybridized labels.

Furthermore, the transcription product of HJURP (e.g., SEQ ID NO: 49) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of HJURP. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degrees C. lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degrees C. for short probes or primers (e.g., 10 to 50 nucleotides) and at least about 60 degrees C. for longer probes or primers. Stringent conditions may also be achieved with the addition of destabilizing substances, such as formamide.

A probe or primer of the present invention is typically a substantially purified oligonucleotide. The oligonucleotide typically includes a region of nucleotide sequence that hybridizes under stringent conditions to at least about 2000, 1000, 500, 400, 350, 300, 250, 200, 150, 100, 50, or 25, consecutive sense strand nucleotide sequence of a nucleic acid including a HJURP sequence, or an anti sense strand nucleotide sequence of a nucleic acid including a HJURP sequence, or of a naturally occurring mutant of these sequences. In particular, for example, in a preferred embodiment, an oligonucleotide having 5-50 in length can be used as a primer for amplifying the genes, to be detected. More preferably, mRNA or cDNA of a HJURP gene can be detected with oligonucleotide probe or primer of a specific size, generally 15-30 b in length. In preferred embodiments, length of the oligonucleotide probe or primer can be selected from 15-25. Assay procedures, devices, or reagents for the detection of gene by using such oligonucleotide probe or primer are well known (e.g. oligonucleotide microarray or PCR). In these assays, probes or primers can also include tag or linker sequences. Further, probes or primers can be modified with detectable label or affinity ligand to be captured. Alternatively, in hybridization based detection procedures, a polynucleotide having a few hundreds (e.g., about 100-200) bases to a few kilo (e.g., about 1000-2000) bases in length can also be used for a probe (e.g., northern blotting assay or cDNA microarray analysis).

Alternatively, the translation product may be detected for the diagnosis of the present invention. For example, the quantity of HJURP protein (SEQ ID NO: 50) or the immunologically fragment thereof may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the HJURP protein. Such antibodies against the peptides of the present invention and the fragments thereof are also provided by the present invention. Methods to prepare these kinds of antibodies for the detection of proteins are well known in the art, and any method may be employed in the present invention to prepare such antibodies and equivalents thereof.

As another method to detect the expression level of HJURP gene based on its translation product, the intensity of staining may be measured via immunohisto-chemical analysis using an antibody against the HJURP protein. Namely, in this measurement, strong staining indicates increased presence/level of the protein and, at the same time, high expression level of HJURP gene.

The expression level of a target gene, e.g., the HJURP gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

© The control level may be determined at the same time as the cancer cells by using a sample(s) previously collected and stored from a subject(s) whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of HJURP gene in samples from subjects whose disease states are known. Furthermore, the control level can be derived from a database of expression patterns from previously tested cells. Moreover, according to an aspect of the present invention, the expression level of HJURP gene in a biological sample may be compared to multiple control levels, determined from multiple reference samples. It is preferred to use a control level determined from a reference sample derived from a tissue type similar to that of the subject-derived biological sample. Moreover, it is preferred to use the standard value of the expression levels of HJURP gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of HJURP gene is increased as compared to the normal control level, or is similar/equivalent to the cancerous control level, the subject may be diagnosed with cancer to be treated.

The present invention also provides a method of (i) diagnosing whether a subject suspected to have cancer to be treated, and/or (ii) selecting a subject for cancer treatment, which method may include the steps of:
a) determining the expression level of HJURP in biological sample (s) obtained from a subject who is suspected to have the cancer to be treated;
b) comparing the expression level of HJURP with a normal control level;
c) diagnosing the subject as having the cancer to be treated, if the expression level of HJURP is increased as compared to the normal control level; and
d) selecting the subject for cancer treatment, if the subject is diagnosed as having the cancer to be treated, in step c).

Alternatively, such a method may include the steps of:
a) determining the expression level of HJURP in biological sample (s) obtained from a subject who is suspected to have the cancer to be treated;
b) comparing the expression level of HJURP with a cancerous control level;
c) diagnosing the subject as having the cancer to be treated, if the expression level of HJURP is similar or equivalent to the cancerous control level; and
d) selecting the subject for cancer treatment, if the subject is diagnosed as having the cancer to be treated, in step c).

The present invention also provides a diagnostic kit for diagnosing or determining a subject who is or is suspected to be suffering from cancer that can be treated with the HJURP polypeptide of the present invention, which may also find use in assessing and/or monitoring the efficacy or applicability of a cancer immunotherapy. Preferably, the cancer includes, but is not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor. More particularly, the kit preferably may include at least one reagent for detecting the expression of the HJURP gene in a subject-derived cell, which reagent may be selected from the group of:
(a) a reagent for detecting mRNA of the HJURP gene;
(b) a reagent for detecting the HJURP protein or the immunologically fragment thereof; and
(c) a reagent for detecting the biological activity of the HJURP protein.

Examples of reagents suitable for detecting mRNA of the HJURP gene may include nucleic acids that specifically bind to or identify the HJURP mRNA, such as oligonucleotides that have a complementary sequence to a portion of the HJURP mRNA. These kinds of oligonucleotides are exemplified by primers and probes that are specific to the HJURP mRNA. These kinds of oligonucleotides may be prepared based on methods well known in the art. If needed, the reagent for detecting the HJURP mRNA may be immobilized on a solid matrix. Moreover, more than one reagent for detecting the HJURP mRNA may be included in the kit.

On the other hand, examples of reagents suitable for detecting the HJURP protein or the immunologically fragment thereof may include antibodies to the HJURP protein or the immunologically fragment thereof. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the HJURP protein or the immunologically fragment thereof. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the HJURP protein may be included in the kit.

The kit may contain more than one of the aforementioned reagents. The kit can further include a solid matrix and reagent for binding a probe against an HJURP gene or antibody against an HJURP peptide, a medium and container for culturing cells, positive and negative control reagents, and a secondary antibody for detecting an antibody against an HJURP peptide. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers may include bottles, vials, and test tubes. The containers may be formed from a variety of materials, such as glass or plastic.

In an embodiment of the present invention, when the reagent is a probe against the HJURP mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of HJURP mRNA present in the sample. The detection sites may be configured in any suitably detectable shape and are typically in the shape of a bar or dot spanning the width of a test strip.

The kit of the present invention may further include a positive control sample or HJURP standard sample. The positive control sample of the present invention may be prepared by collecting HJURP positive samples and then assaying their HJURP levels. Alternatively, a purified HJURP protein or polynucleotide may be added to cells that do not express HJURP to form the positive sample or the HJURP standard sample. In the present invention, purified HJURP may be a recombinant protein. The HJURP level of the positive control sample is, for example, more than the cut off value.

In one embodiment, the present invention further provides a diagnostic kit including, a protein or a partial protein thereof capable of specifically recognizing the antibody of the present invention or the fragment thereof.

Examples of the partial peptide of the protein of the present invention include polypeptides composed of at least 8, preferably 15, and more preferably 20 contiguous amino acids in the amino acid sequence of the protein of the present invention. Cancer can be diagnosed by detecting an antibody in a sample (e.g., blood, tissue) using a protein or a peptide (polypeptide) of the present invention. The method for preparing the protein of the present invention and peptides are as described above.

The methods for diagnosing cancer of the present invention can be performed by determining the difference between the amount of anti-HJURP antibody and that in the corresponding control sample as describe above. The subject is suspected to be suffering from cancer, if biological samples of the subject contain antibodies against the expression products (HJURP) of the gene and the quantity of the anti-HJURP antibody is determined to be more than the cut off value in level compared to that in normal control.

In another embodiment, a diagnostic kit of the present invention may include the peptide of the present invention and an HLA molecule binding thereto. The method for detecting antigen specific CTLs using antigenic peptides and HLA molecules has already been established (for example, Altman J D et al., Science. 1996, 274(5284): 94-6). Thus, the complex of the peptide of the present invention and the HLA molecule can be applied to the detection method to detect tumor antigen specific CTLs, thereby enabling earlier detection, recurrence and/or metastasis of cancer. Further, it can be employed for the selection of subjects applicable with the pharmaceuticals including the peptide of the present invention as an active ingredient, or the assessment of the treatment effect of the pharmaceuticals.

Particularly, according to the known method (see, for example, Altman J D et al., Science. 1996, 274(5284): 94-6), the oligomer complex, such as tetramer, of the radiolabeled HLA molecule and the peptide of the present invention can be prepared. With using the complex, the diagnosis can be done, for example, by quantifying the antigen-peptide specific CTLs in the peripheral blood lymphocytes derived from the subject suspected to be suffering from cancer.

The present invention further provides a method or diagnostic agents for evaluating immunological response of subject by using peptide epitopes as described herein. In one embodiment of the invention, HLA-A24, or HLA-A02 restricted peptides as described herein may be used as reagents for evaluating or predicting an immune response of a subject. The immune response to be evaluated may be induced by contacting an immunogen with immunocompetent cells in vitro or in vivo. In preferred embodiments, the immunocompetent cells for evaluating an immunological response, may be selected from among peripheral blood, peripheral blood lymphocyte (PBL), and peripheral blood mononuclear cell (PBMC). Methods for collecting or isolating such immunocompetent cells are well known in the arts. In some embodiments, any substances or compositions that may result in the production of antigen specific CTLs that recognize and bind to the peptide epitope(s) may be employed as the reagent. The peptide reagents may need not to be used as the immunogen. Assay systems that are used for such an analysis include relatively recent technical developments such as tetramers, staining for intracellular lymphokines and interferon release assays, or ELISPOT assays. In a preferred embodiment, immunocompetent cells to be contacted with peptide reagent may be antigen presenting cells including dendritic cells.

For example, peptides of the present invention may be used in tetramer staining assays to assess peripheral blood mononuclear cells for the presence of antigen-specific CTLs following exposure to a tumor cell antigen or an immunogen. The HLA tetrameric complex may be used to directly visualize antigen specific CTLs (see, e.g., Ogg et al., Science 279: 2103-2106, 1998; and Altman et al, Science 174: 94-96, 1996) and determine the frequency of the antigen-specific CTL population in a sample of peripheral blood mononuclear cells. A tetramer reagent using a peptide of the invention may be generated as described below.

A peptide that binds to an HLA molecule is refolded in the presence of the corresponding HLA heavy chain and beta 2-microglobulin to generate a trimolecular complex. In the complex, carboxyl terminal of the heavy chain is biotinylated at a site that was previously engineered into the protein. Then, streptavidin is added to the complex to form tetramer composed of the trimolecular complex and streptavidin. By means of fluorescently labeled streptavidin, the tetramer can be used to stain antigen specific cells. The cells can then be identified, for example, by flow cytometry. Such an analysis may be used for diagnostic or prognostic purposes. Cells identified by the procedure can also be used for therapeutic purposes.

The present invention also provides reagents to evaluate immune recall responses (see, e.g., Bertoni et al, J. Clin. Invest. 100: 503-513, 1997 and Penna et al., J Exp. Med. 174: 1565-1570, 1991) including peptides of the present invention. For example, patient PBMC samples from individuals with cancer to be treated can be analyzed for the presence of antigen-specific CTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL activity.

The peptides may also be used as reagents to evaluate the efficacy of a vaccine. PBMCs obtained from a patient vaccinated with an immunogen may be analyzed using, for example, either of the methods described above. The patient is HLA typed, and peptide epitope reagents that recognize the allele-specific molecules present in the patient are selected for the analysis. The immunogenicity of the vaccine may be indicated by the presence of epitope-specific CTLs in the PBMC sample. The peptides of the invention may also be used to make antibodies, using techniques well known in the art (see, e.g., CURRENT PROTOCOLS IN IMMUNOLOGY, Wiley/Greene, NY; and Antibodies A Laboratory Manual, Harlow and Lane, Cold Spring Harbor Laboratory Press, 1989), which may find use as reagents to diagnose, detect or monitor cancer. Such antibodies may include those that recognize a peptide in the context of an HLA molecule, i.e., antibodies that bind to a peptide-MHC complex.

The peptides and compositions of the present invention have a number of additional uses, some of which are described herein For instance, the present invention provides a method for diagnosing or detecting a disorder characterized by expression or presentation of a HJURP immunogenic polypeptide. These methods involve determining expression or presentation of a HJURP HLA binding peptide, or a complex of a HJURP HLA binding peptide and an HLA class I molecule in a biological sample. The expression or presentation of a peptide or complex of peptide and HLA class I molecule can be determined or detected by assaying with a binding partner for the peptide or complex. In a preferred embodiment, a binding partner for the peptide or complex may be an antibody recognizes and specifically bind to the peptide or the complex. The expression of HJURP in a biological sample, such as a tumor biopsy, can also be tested by standard PCR amplification protocols using HJURP primers. An example of tumor expression is presented herein and further disclosure of exemplary conditions and primers for HJURP amplification can be found in WO2003/27322.

Preferably, the diagnostic methods involve contacting a biological sample isolated from a subject with a substance specific for the HJURP HLA binding peptide to detect the presence of the HJURP HLA binding peptide in the biological sample. As used herein, "contacting" means placing the biological sample in sufficient proximity to the agent and under the appropriate conditions of, e.g., concentration, temperature, time, ionic strength, to allow the specific interaction between the agent and HJURP HLA binding peptide that are present in the biological sample. In general, the conditions for contacting the agent with the biological sample are conditions known by those of ordinary skill in the art to facilitate a specific interaction between a molecule and its cognate (e.g., a protein and its receptor cognate, an antibody and its protein antigen cognate, a nucleic acid and its complementary sequence cognate) in a biological sample. Exemplary conditions for facilitating a specific interaction between a molecule and its cognate are described in U.S. Pat. No. 5,108,921, issued to Low et al.

The diagnostic method of the present invention can be performed in either or both of in vivo and in vitro. Accordingly, biological sample can be located in vivo or in vitro in the present invention. For example, the biological sample can be a tissue in vivo and the agent specific for the HJURP immunogenic polypeptide can be used to detect the presence of such molecules in the tissue. Alternatively, the biological sample can be collected or isolated in vitro (e.g., a blood sample, tumor biopsy, tissue extract). In a particularly preferred embodiment, the biological sample can be a cell-containing sample, more preferably a sample containing tumor cells collected from a subject to be diagnosed or treated.

Alternatively, the diagnosis can be done, by a method which allows direct quantification of antigen-specific T cells by staining with Fluorescein-labeled HLA multimeric complexes (e.g., Altman, J. D. et al., 1996, Science 274: 94; Altman, J. D. et al., 1993, Proc. Natl. Acad. Sci. USA 90: 10330). Staining for intracellular lymphokines, and interferon-gamma release assays or ELISPOT assays also has been provided. Multimer staining, intracellular lymphokine staining and ELISPOT assays all appear to be at least 10-fold more sensitive than more conventional assays (Murali-Krishna, K. et al., 1998, Immunity 8: 177; Lalvani, A. et al., 1997, J. Exp. Med. 186: 859; Dunbar, P. R. et al., 1998, Curr. Biol. 8: 413). Pentamers (e.g., US 2004-209295A), dextramers (e.g., WO 02/072631), and streptamers (e.g., Nature medicine 6. 631-637 (2002)) may also be used.

For instance, in some embodiments, the present invention provides a method for diagnosing or evaluating an immunological response of a subject administered at least one of HJURP peptides of the present invention, the method including the steps of:

(a) contacting an immunogen with immunocompetent cells under the condition suitable of induction of CTL specific to the immunogen;

(b) detecting or determining induction level of the CTL induced in step (a); and (c) correlating the immunological response of the subject with the CTL induction level.

In the present invention, the immunogen is at least one of (a) a HJURP peptide selected from among the amino acid sequences of SEQ ID NOs: 2 to 24 and 26 to 48, peptides having such amino acid sequences, and peptides having in which such amino acid sequences have been modified with 1, 2 or more amino acid substitution(s). In the meantime, conditions suitable of induction of immunogen specific CTL are well known in the art. For example, immunocompetent cells may be cultured in vitro under the presence of immunogen(s) to induce immunogen specific CTL. In order to induce immunogen specific CTLs, any stimulating factors may be added to the cell culture. For example, IL-2 is preferable stimulating factors for the CTL induction.

In some embodiments, the step of monitoring or evaluating immunological response of a subject to be treated with peptide cancer therapy may be performed before, during and/or after the treatment. In general, during a protocol of cancer therapy, immunogenic peptides are administered repeatedly to a subject to be treated. For example, immunogenic peptides may be administered every week for 3-10 weeks. Accordingly, the immunological response of the subject can be evaluated or monitored during the cancer therapy protocol. Alternatively, the step of evaluation or monitoring of immunological response to the cancer therapy may at the completion of the therapy protocol.

According to the present invention, enhanced induction of immunogen specific CTL as compared with a control indicates that the subject to be evaluated or diagnosed immunologically responded to the immunogen(s) that has/have been administered. Suitable controls for evaluating the immunological response may include, for example, a CTL induction level when the immunocompetent cells are contacted with no peptide, or control peptide(s) having amino acid sequences other than any HJURP peptides. (e.g. random amino acid sequence). In a preferred embodiment, the immunological response of the subject is evaluated in a sequence specific manner, by comparison with an immunological response between each immunogen administered to the subject. In particular, even when a mixture of some kinds of HJURP peptides is administered to the subject, immunological response might vary depending on the peptides. In that case, by comparison of the immunological response between each peptide, peptides to which the subject show higher response can be identified.

XI. Antibodies

The present invention further provides antibodies that bind to the peptides of the present invention. Preferred antibodies specifically bind to the peptide of the present invention and will not bind (or will bind weakly) to non-peptide of the present invention. Alternatively, antibodies bind to the peptide of the invention as well as the homologs thereof. Antibodies against the peptide of the invention can find use in cancer diagnostic and prognostic assays, and imaging methodologies. Similarly, such antibodies can find use in the treatment, diagnosis, and/or prognosis of other cancers, to the extent HJURP is also expressed or overexpressed in cancer patient. Moreover, intracellularly expressed antibodies (e.g., single chain antibodies) may therapeutically find use in treating cancers in which the expression of HJURP is involved, examples of which include, but are not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention also provides various immunological assay for the detection and/or quantification of HJURP protein (SEQ ID NO: 50) or fragments thereof including a polypeptide having an amino acid sequence selected from among SEQ ID NOs: 2 to 24 and 26 to 48. Such assays may include one or more anti-HJURP antibodies capable of recognizing and binding a HJURP protein or fragments thereof, as appropriate. In the present invention, anti-HJURP antibodies binding to HJURP polypeptide preferably recognize a polypeptide having an amino acid sequenceselected from among SEQ ID NOs: 2 to 24 and 26 to 48. A binding specificity of antibody can be confirmed with inhibition test. That is, when the binding between an antibody to be analyzed and full-length of HJURP polypeptide are inhibited under presence of any fragment polypeptides having an amino acid sequence selected from among SEQ ID NOs: 2 to 24 and 26 to 48, the antibody specifically binds to the fragment. In the present invention, such immunological assays are performed within various immunological assay formats well known in the art, including but not limited to, various types of radio-immunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MEW binding assays.

In addition, immunological imaging methods capable of detecting cancers expressing HJURP are also provided by the invention, including, but not limited to, radioscintigraphic imaging methods using labeled antibodies of the present invention. Such assays can clinically find use in the detection, monitoring, and prognosis of HJURP expressing cancers including, but not limited to, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention also provides an antibody that binds to the peptide of the invention. The antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, the peptide to be used as an immunization antigen may be a complete protein or a partial peptide of the protein. A partial peptide may include, for example, the amino (N)-terminal or carboxy (C)-terminal fragment of a peptide of the present invention.

Herein, an antibody is defined as a protein that reacts with either the full length or a fragment of a HJURP peptide. In a preferred embodiment, antibody of the present invention can recognize fragment peptides of HJURP having an amino acid sequence selected from among SEQ ID NOs: 2 to 24 and 26 to 48. Methods for synthesizing oligopeptide are well known in the arts. After the synthesis, peptides may be optionally purified prior to use as immunogen. In the present invention, the oligopeptide (e.g., 9- or 10 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, but preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, in which a non-human animal is immunized with an antigen for preparing hybridoma, human lymphocytes such as those infected by EB virus may be immunized with a peptide, peptide expressing cells or their lysates in vitro. Then, the immunized lymphocytes are fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the peptide of the present invention is coupled. The antibody of the present invention can be used not only for purification and detection of the peptide of the present invention, but also as a candidate for agonists and antagonists of the peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides a vector and host cell into which a nucleotide encoding the peptide of the present invention is introduced. A vector of the present invention can find use to keep a nucleotide, especially a DNA, of the present invention in host cell, to express the peptide of the present invention, or to administer the nucleotide of the present invention for gene therapy.

When *E. coli* is a host cell and the vector is amplified and produced in a large amount in *E. coli* (e.g., JM109, DH5 alpha, HB101 or XL1Blue), the vector should have "ori" to be amplified in *E. coli* and a marker gene for selecting transformed *E. coli* (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in *E. coli* should have the above characteristics to be amplified in *E. coli*. When *E. coli*, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The following examples are presented to illustrate the present invention and to assist one of ordinary skill in making and using the same. The examples are not intended in any way to otherwise limit the scope of the invention.

EXAMPLE

Example 1

Materials and Methods
Cell Lines
TISI, HLA-A*2402-positive B-lymphoblastoid cell line, was purchased from the IHWG Cell and Gene Bank (Seattle, Wash.). COS7, African green monkey kidney cell line, was purchased from ATCC.

Candidate Selection of Peptides Derived from Hjurp
9-mer and 10-mer peptides derived from HJURP that bind to HLA-A*2402 molecule were predicted using binding prediction software "BIMAS" (www bimas.cit.nih.gov/molbio/hla_bind) (Parker et al. (J Immunol 1994, 152(1): 163-75), Kuzushima et al. (Blood 2001, 98(6): 1872-81)) and "NetMHC 3.0" (www.cbs.dtu.dk/services/NetMHC/) (Buus et al. (Tissue Antigens., 62:378-84, 2003), Nielsen et al. (Protein Sci., 12:1007-17, 2003, Bioinformatics, 20(9): 1388-97, 2004)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*2402 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (GM-CSF) (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTL was tested against peptide-pulsed TISI cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell SR et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed TISI ($1 \times 10^4$ cells/well) was prepared as stimulator cells. Cultured cells in 48 wells were used as responder cells. IFN-gamma ELISPOT assay and IFN-gamma ELISA assay were performed under manufacture procedure.

Plasmid Transfection

The cDNA encoding an open reading frame of target genes or HLA-A*2402 was amplified by PCR. The PCR-amplified products were cloned into a vector and pIRES vector (Clontech Laboratories, Inc., Cat. No. 631605). The plasmids were transfected into COS7, which is the target genes and HLA-A24 negative cell line, using lipofectamine 2000 (Invitrogen) according to the manufacturer's recommended procedures. After 2 days from transfection, the transfected cells were harvested with versene (Invitrogen) and used as the target cells ($5 \times 10^4$ cells/well) for CTL activity assay.

Results

Enhanced HJURP Expression in Cancers

The global gene expression profile data obtained from various cancers using cDNA-microarray revealed that HJURP (GenBank Accession No. NM_018410; SEQ ID No: 49) expression was elevated. HJURP expression was validly elevated in 3 out of 15 AMLs, 25 out of 26 bladder cancers, 29 out of 33 breast cancers, 8 out of 9 cervical cancers, 11 out of 11 cholangiocellular carcinoma, 25 out of 33 CMLs, 4 out of 12 colorectal cancers, 29 out of 40 esophagus cancers, 1 out of 3 gastric cancer diffused-type, 4 out of 4 liver cancer, 12 out of 12 NSCLC, 2 out of 3 lymphoma, 8 out of 11 osteosarcomas, 3 out of 5 ovarian cancer, 4 out of 4 pancreatic cancer, 12 out of 18 prostate cancer, 4 out of 7 renal carcinomas, 13 out of 13 SCLC, 8 out of 14 soft tissue tumor and 6 out of 9 testicular tumor as compared with corresponding normal tissue (Table 1).

TABLE 1

Ratio of cases observed up-regulation of HJIJRP in cancerous tissue as compared with pphnormal corresponding tissue

| | |
|---|---|
| AML | 3/15 |
| Bladder cancer | 25/26 |
| Breast cancer | 29/33 |
| Cervical cancer | 8/9 |
| Cholangiocellular carcinoma | 11/11 |
| CML | 25/33 |
| Colorectal cancer | 4/12 |
| Esophagus cancer | 29/40 |
| Gastric cancer Diffused-type | 1/3 |
| Liver cancer | 4/4 |
| NSCLC | 12/12 |
| Lymphoma | 2/3 |

TABLE 1-continued

Ratio of cases observed up-regulation of HJURP in cancerous tissue as compared with ppnormal corresponding tissue

| | |
|---|---|
| Osteosarcoma | 8/11 |
| Ovarian cancer | 3/5 |
| Pancreatic cancer | 4/4 |
| Prostate cancer | 12/18 |
| Renal carcinoma | 4/7 |
| SCLC | 13/13 |
| Soft tissue tumor | 8/14 |
| Testicular tumor | 6/9 |

Prediction of HLA-A24 Binding Peptides Derived from HJURP

Tables 2a and 2b shows the HLA-A24 binding 9 mer and 10 mer peptides of HJURP in the order of high binding affinity. 15 peptides (SEQ ID NO: 1-6 and SEQ ID NO: 10-18) were selected by using BIMAS, and 9 peptides (SEQ ID NO: 7-9 and SEQ ID NO: 19-24) were predicted by NetMHC3.0. A total of 24 peptides with potential HLA-A24 binding ability were selected and examined to determine the epitope peptides.

TABLE 2

HLA-A24 binding 9 mer peptides derived from HJURP

| Start Position | amino acid sequence | Score | SEQ ID NO |
|---|---|---|---|
| 149 | KYLTQVDIL | 600 | 1 |
| 576 | RYDEIKEEF | 369.5 | 2 |
| 28 | RFQRRMQRL | 72 | 3 |
| 263 | LYAGMLHSM | 25 | 4 |
| 403 | RFRTLKWLI | 12 | 5 |
| 388 | IYFDSSATY | 6 | 6 |

| Start Position | amino acid sequence | Kd (nM) | SEQ ID NO |
|---|---|---|---|
| 408 | KWLISPVKI | 55 | 7 |
| 544 | VQGNSSGIF | 3458 | 8 |
| 280 | SSIISTKTF | 6673 | 9 |

TABLE 2b

HLA-A24 binding 10 mer peptides derived from HJURP

| Start Position | amino acid sequence | score | SEQ ID NO |
|---|---|---|---|
| 149 | KYLTQVDILL | 840 | 10 |
| 395 | TYNLDEENRF | 180 | 11 |
| 729 | SYRMEEKSDF | 100 | 12 |
| 56 | TYETPQGLRI | 75 | 13 |
| 590 | KYCLKSPGQM | 50 | 14 |
| 635 | GFQKLPSSPL | 30 | 15 |
| 389 | YFDSSATYNL | 20 | 16 |
| 28 | RFQRRMQRLI | 15 | 17 |
| 383 | KYSSLIYFDS | 14 | 18 |

| Start Position | amino acid sequence | Kd (nM) | SEQ ID NO |
|---|---|---|---|
| 379 | VTPSKYSSLI | 458 | 19 |
| 235 | SLQETSSSSF | 8454 | 20 |
| 218 | LHPSSTDMAL | 13453 | 21 |
| 388 | IYFDSSATYN | 13358 | 22 |
| 162 | EYFECAGNRA | 14992 | 23 |
| 627 | LNPDPHFQGF | 19791 | 24 |

Start position indicates the number of amino acid residue from the N-terminus of HJURP. Binding score and dissociation constant [Kd (nM)] are derived from "BIMAS" and "NetMHC3.0".

CTL Induction with the Predicted Peptides from HJURP Restricted with HLA-A*2402 and Establishment for CTL Lines Stimulated with HJURP Derived Peptides CTLs for those peptides derived from HJURP were generated according to the protocols as described in "Materials and Methods". Peptide specific CTL activity was determined by IFN-gamma ELISPOT assay (FIGS. 1a-e). Well number #4 with HJURP-A24-9-28 (SEQ ID NO: 3) (a), #4 with HJURP-A24-9-263 (SEQ ID NO: 4) (b), #4 with HJURP-A24-9-408 (SEQ ID NO: 7) (c), #6 with HJURP-A24-10-383 (SEQ ID NO: 18) (d) and #4 with HJURP-A24-10-162 (SEQ ID NO: 23) (e) demonstrated potent IFN-gamma production as compared to the control wells. On the other hand, no potent IFN-gamma production could be detected by stimulation with other peptides shown in Tables 2a and 2b, despite those peptides had possible binding activity with HLA-A*2402. As is typical of negative data, a specific CTL response was not observed from the peptide-pulsed target cellsstimulated with HJURP-A24-9-149 (SEQ ID NO: 1) (f). As a result, 5 peptides derived from HJURP were identified as having the potential to induce potent CTLs.

Establishment of CTL Lines and Clones Against HJURP Specific Peptides

Figure 3:
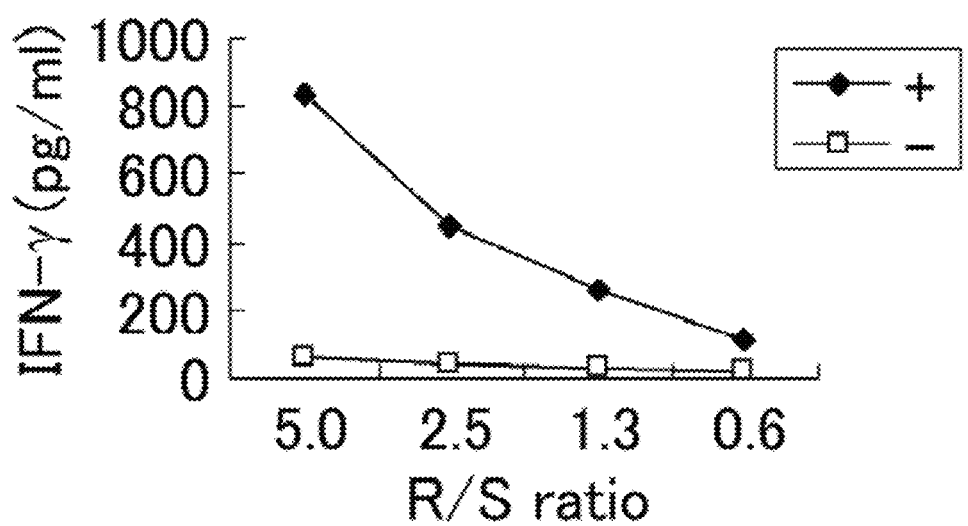
FIG. 3 is a line graph depicting the IFN-gamma production of a CTL clone established by limiting dilution from the CTL line stimulated with HJURP-A24-9-408 (SEQ ID NO: 7). The results demonstrate that the CTL clone established by stimulation with HJURP-A24-9-408 (SEQ ID NO: 7) show potent IFN-gamma production compared with the control. In the figure, "+" indicates the IFN-gamma production against target cells pulsed with the each peptide and "−" indicates the IFN-gamma production against target cells not pulsed with any peptides.

The cells that showed peptide specific CTL activity detected by IFN-gamma ELISPOT assay in the well number #4 with HJURP-A24-9-263 (SEQ ID NO: 4) and in #4 with HJURP-A24-9-408 (SEQ ID NO: 7) were expanded and CTL lines were established by limiting dilution as described in the "Materials and Methods" section above. CTL activity of those CTL lines was determined by IFN-gamma ELISA assay (FIGS. 2a and b). The CTL lines demonstrated potent IFN-gamma production against the target cells pulsed with corresponding peptide as compared to target cells without peptide pulse. Furthermore, CTL clone was established by limiting dilution from the CTL line, and IFN-gamma production from CTL clone against target cells pulsed peptide was determined by IFN-gamma ELISA assay. Potent IFN-gamma production was determined from CTL clone stimulated with HJURP-A24-9-408 (SEQ ID NO: 7) in FIG. 3.

Specific CTL Activity Against Target Cells Exogenously Expressing HJURP and HLA-A*2402

Figure 4A:
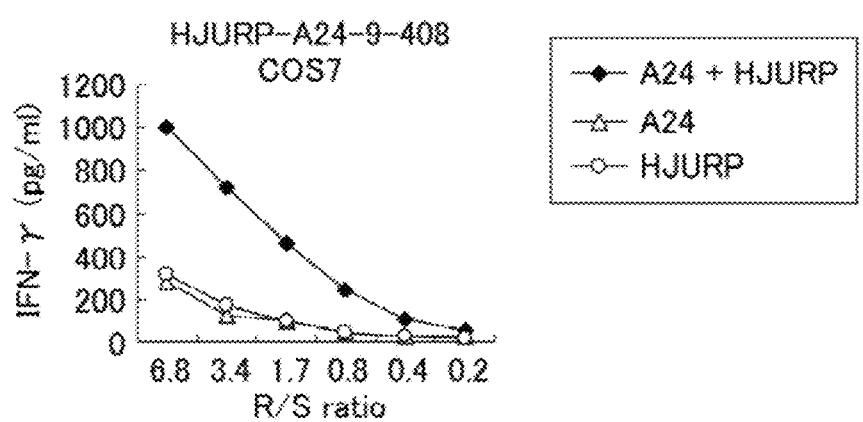
FIGS. 4A-4B is composed of a series of line graphs depicting specific CTL activity against the target cells that exogenously express HJURP and HLA-A*2402. COS7 cells transfected with HLA-A*2402 or with the full length HJURP gene were prepared as controls. The CTL line established with HJURP-A24-9-408 (SEQ ID NO: 7) (FIG. 4A) and HJURP-A24-9-263 (SEQ ID NO: 4) (FIG. 4B) showed specific CTL activity against COS7 cells transfected with both HJURP and HLA-A*2402 (black lozenge). On the other hand, no significant specific CTL activity was detected against target cells expressing either HLA-A*2402 (triangle) or HJURP (circle).
Figure 4B:
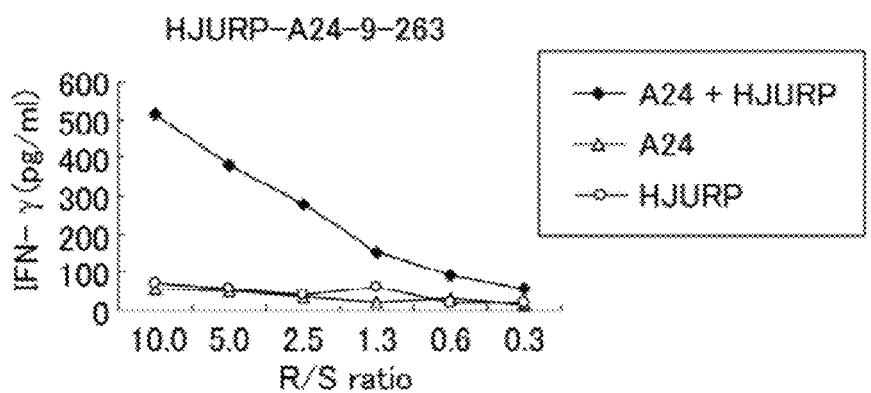
Figure 6A:
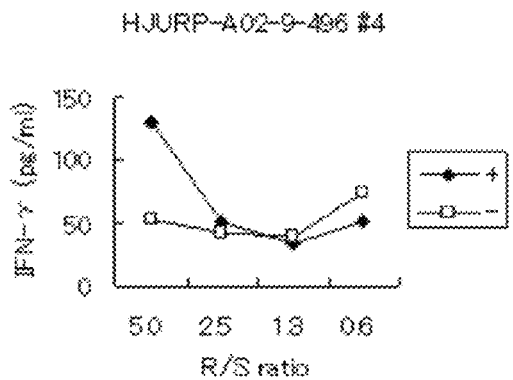
FIGS. 6A-6E is composed of a series of line graphs depicting the results of an IFN-gamma ELISA assay demonstrating the IFN-gamma production of the CTL lines stimulated with HJURP-A02-9-496 (SEQ ID NO: 26) (FIG. 6A), HJURP-A02-9-406 (SEQ ID NO: 30) (FIG. 6B), HJURP-A02-9-129 (SEQ ID NO: 31) (FIG. 6C), HJURP-A02-10-405 (SEQ ID NO: 37) (FIG. 6D) and HJURP-A02-10-128 (SEQ ID NO: 38) (FIG. 6E). The results demonstrate that CTL lines established by stimulation with each peptide show potent IFN-gamma production as compared with the control. In the figures, "+" indicates the IFN-gamma production against target cells pulsed with the appropriate peptide and "−" indicates the IFN-gamma production against target cells not pulsed with any peptides.
Figure 6B:
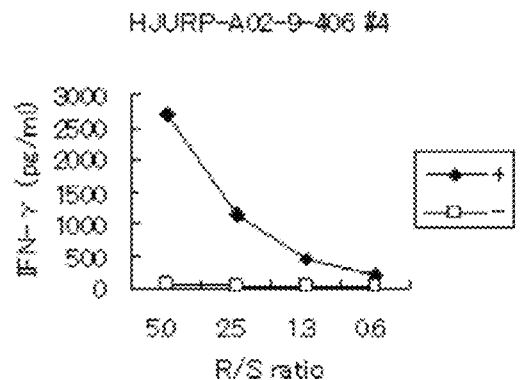
Figure 6C:
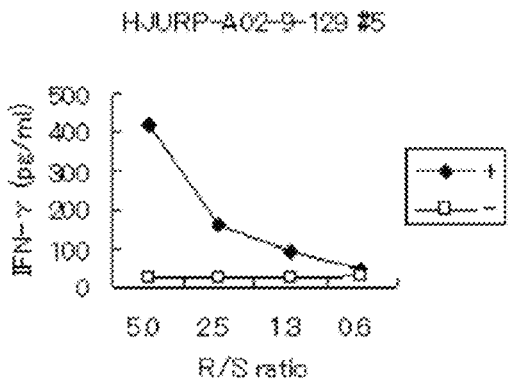
Figure 6D:
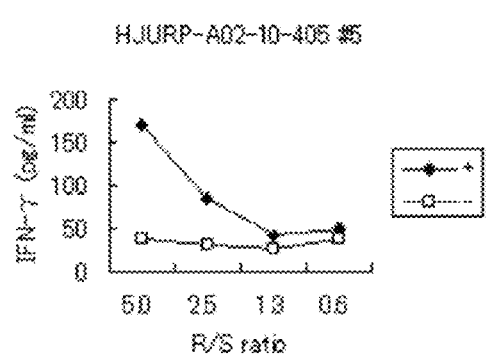
Figure 6E:
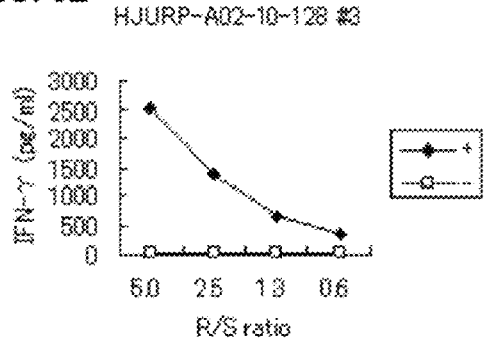
Figure 7A:
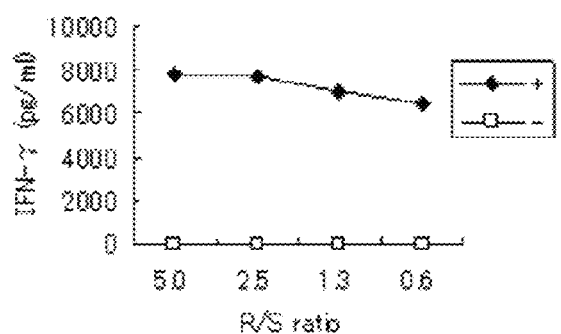
FIGS. 7A-7D is composed of a series of line graphs depicting the IFN-gamma production of the CTL clones established by limiting dilution from the CTL lines stimulated with HJURP-A02-9-406 (SEQ ID NO: 30) (FIG. 7A), HJURP-A02-9-129 (SEQ ID NO: 31) (FIG. 7B), HJURP-A02-10-405 (SEQ ID NO: 37) (FIG. 7C) and HJURP-A02-10-128 (SEQ ID NO: 38) (FIG. 7D). The results demonstrate that the CTL clones established by stimulation with each peptide showed potent IFN-gamma production compared with the control. In the figure, "+" indicates the IFN-gamma production against target cells pulsed with the each peptide and "−" indicates the IFN-gamma production against target cells not pulsed with any peptides.
Figure 7B:
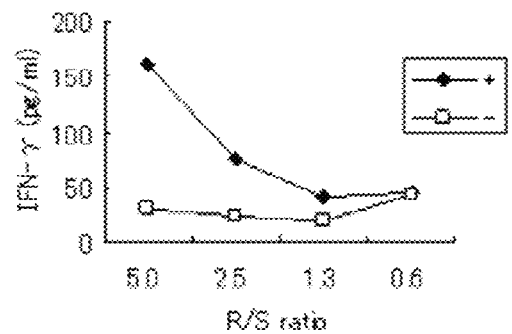
Figure 7C:
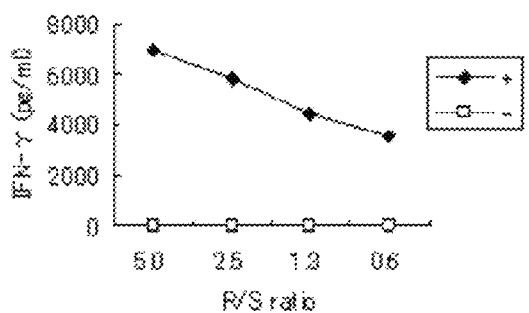
Figure 7D:
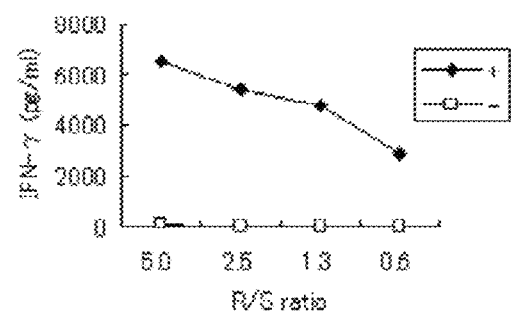

The established CTL line raised against these peptides were examined for their ability to recognize target cells that endogenously express HJURP and HLA-A*2402 gene. Specific CTL activity against COS7 cells which transfected with both the full length of HJURP and HLA-A*2402 gene (a specific model for the target cells that endogenously express HJURP and HLA-A*2402 gene) was tested using the CTL lines raised by corresponding peptide as the effector cells. COS7 cells transfected with either full length of HJURP genes or HLA-A*2402 were prepared as controls. In FIG. 4, the CTLs stimulated with HJURP-A24-9-408 (SEQ ID NO: 7) (a) and HJURP-A24-9-263 (SEQ ID NO: 4) (b) showed potent CTL activity against COS7 cells expressing both HJURP and HLA-A*2402. On the other hand, no significant specific CTL activity was detected against the controls. Thus, these data clearly demonstrated that peptides of HJURP-A24-9-408 (SEQ ID NO: 7) and HJURP-A24-9-263 (SEQ ID NO: 4) were endogenously processed and expressed on the target cells with HLA-A*2402 molecule and were recognized by the CTLs. These results indicate that this peptide derived from HJURP may be suitable as a cancer vaccine for the treatment of patients with HJURP expressing tumors.

Homology Analysis of Antigen Peptides

The CTLs stimulated with HJURP-A24-9-28 (SEQ ID NO: 3), HJURP-A24-9-263 (SEQ ID NO: 4), HJURP-A24-

9-408 (SEQ ID NO: 7), HJURP-A24-10-383 (SEQ ID NO: 19) and HJURP-A24-10-162 (SEQ ID NO: 23) showed significant and specific CTL activity. This result may be due to the fact that the sequences of HJURP-A24-9-28 (SEQ ID NO: 3), HJURP-A24-9-263 (SEQ ID NO: 4), HJURP-A24-9-408 (SEQ ID NO: 7), HJURP-A24-10-383 (SEQ ID NO: 18) and HJURP-A24-10-162 (SEQ ID NO: 23) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequences of HJURP-A24-9-28 (SEQ ID NO: 3), HJURP-A24-9-263 (SEQ ID NO: 4), HJURP-A24-9-408 (SEQ ID NO: 7), HJURP-A24-10-383 (SEQ ID NO: 18) and HJURP-A24-10-162 (SEQ ID NO: 23) are unique and thus, there is little possibility, to our best knowledge, that these molecules raise unintended immunologic response to some unrelated molecule.

In conclusion, novel HLA-A24 epitope peptide derived from HJURP were identified. Furthermore, the results herein demonstrate that epitope peptide of HJURP may be suitable for use in for cancer immunotherapy.

Examples 2

Materials and Methods

Cell Lines

T2, HLA-A*0201-positive B-lymphoblastoid cell line, and COS7, African green monkey kidney cell line, were purchased from ATCC.

Candidate Selection of Peptides Derived from HJURP 9-mer and 10-mer peptides derived from HJURP that bind to HLA-A*0201 molecule were predicted using binding prediction software "NetMHC 3.0" (www.cbs.dtu.dk/services/NetMHC/) (Buus et al. (Tissue Antigens., 62:378-84, 2003), Nielsen et al. (Protein Sci., 12:1007-17, 2003, Bioinformatics, 20(9):1388-97, 2004)). These peptides were synthesized by Biosynthesis (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethyl-sulfoxide (DMSO) at 20 mg/ml and stored at −80 degrees C.

In Vitro CTL Induction

Monocyte-derived dendritic cells (DCs) were used as antigen-presenting cells to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1,000 U/ml of granulocyte-macrophage colony-stimulating factor (R&D System) and 1,000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 micro-g/ml of each of the synthesized peptides in the presence of 3 micro-g/ml of beta 2-microglobulin for 3 hrs at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by X-irradiation (20 Gy) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On days 7 and 14, the T cells were further stimulated with the autologous peptide-pulsed DCs. The DCs were prepared each time by the same way described above. CTLs were tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by Mitomycin C, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Establishment of CTL Clones

The dilutions were made to have 0.3, 1, and 3 CTLs/well in 96 round-bottomed micro titer plate (Nalge Nunc International). CTLs were cultured with $1 \times 10^4$ cells/well of 2 kinds of human B-lymphoblastoid cell lines, 30 ng/ml of anti-CD3 antibody, and 125 U/ml of IL-2 in a total of 150 micro-l/well of AIM-V Medium containing 5% AS. 50 micro-l/well of IL-2 were added to the medium 10 days later so to reach a final concentration of 125 U/ml IL-2. CTL activity was tested on the 14th day, and CTL clones were expanded using the same method as described above (Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1 \times 10^4$/well) was prepared as stimulator cells. Cultured cells in 48 wells were used as responder cells. IFN-gamma ELISPOT assay and IFN-gamma ELISA assay were performed under manufacture procedure.

Establishment of the Cells Forcibly Expressing Either or Both of the Target Gene and HLA-A02

The cDNA encoding an open reading frame of target genes or HLA-A*0201 was amplified by PCR. The PCR-amplified products were cloned into pIRES vector (Clontech Laboratories, Inc., Cat. No. 631605). The plasmids were transfected into COS7, which is the target genes and HLA- A02-negative cell line, using lipofectamine 2000 (Invitrogen) according to the manufacturer's recommended procedures. After 2 days from transfection, the transfected cells were harvested with versene (Invitrogen) and used as the target cells ($5×10^4$ cells/well) for CTL activity assay.

Results

Prediction of HLA-A*0201 Binding Peptides Derived from HJURP

Tables 3a and 3b show the HLA-A2 binding 9 mer and 10 mer peptides of HJURP in the order of high binding affinity. A total of 24 peptides with potential HLA-A2 binding ability were selected and examined to determine the epitope peptides.

TABLE 3a

HLA-A2 binding 9 mer peptides derived from HJURP

| Start Position | amino acid sequence | Kd (nM) | SEQ ID NO |
|---|---|---|---|
| 150 | YLTQVDILL | 14 | 25 |
| 496 | SLSEAFENL | 21 | 26 |
| 354 | KLEKAFLEV | 52 | 27 |
| 266 | GMLHSMSRL | 84 | 28 |
| 51 | QMATLTYET | 100 | 29 |
| 406 | TLKWLISPV | 118 | 30 |
| 129 | VAWALAPAV | 135 | 31 |
| 599 | MTVPLCIGV | 153 | 32 |
| 226 | ALVPRNDSL | 204 | 33 |
| 274 | LLSTKPSSI | 305 | 34 |
| 386 | SLIYFDSSA | 324 | 35 |
| 244 | FLSSQPFED | 5111 | 36 |

TABLE 3b

HLA-A2 binding 10 mer peptides derived from HJURP

| Start Position | amino acid sequence | Kd (nM) | SEQ ID NO |
|---|---|---|---|
| 405 | RTLKWLISPV | 15 | 37 |
| 128 | SVAWALAPAV | 50 | 38 |
| 649 | SLLGSTAIEA | 75 | 39 |
| 273 | RLLSTKPSSI | 167 | 40 |
| 266 | GMLHSMSRLL | 240 | 41 |
| 598 | QMTVPLCIGV | 246 | 42 |
| 54 | TLTYETPQGL | 281 | 43 |
| 731 | RMEEKSDFML | 366 | 44 |
| 397 | NLDEENRFRT | 2637 | 45 |
| 157 | LLQGAEYFEC | 3384 | 46 |
| 455 | RMCLPDSWAM | 5539 | 47 |
| 156 | ILLQGAEYFE | 14204 | 48 |

Start position indicates the number of amino acid residue from the N-terminus of HJURP. Dissociation constant [Kd (nM)] are derived from "NetMHC3.0".

CTL Induction with the Predicted Peptides from HJURP Restricted with HLA-A*0201 and Establishment for CTL Lines Stimulated with HJURP Derived Peptides CTLs for those peptides derived from HJURP were generated according to the protocols as described in "Materials and Methods". Peptide specific CTL activity was determined by IFN-gamma ELISPOT assay (FIGS. 5a-i). The following wells demonstrated potent IFN-gamma production as compared to the control wells: number #4 stimulated with HJURP-A02-9-496 (SEQ ID NO: 26) (a), #2 with HJURP-A02-9-354 (SEQ ID NO: 27) (b), #4 with HJURP-A02-9-406 (SEQ ID NO: 30) (c), #5 with HJURP-A02-9-129 (SEQ ID NO: 31) (d), #3 with HJURP-A02-9-599 (SEQ ID NO: 32) (e), #1 with HJURP-A02-9-386 (SEQ ID NO: 35) (f), #5 with HJURP-A02-10-405 (SEQ ID NO: 37) (g), #3 with HJURP-A02-10-128 (SEQ ID NO: 38) (h) and #6 with HJURP-A02-10-54 (SEQ ID NO: 43) (i). On the other hand, no potent IFN-gamma production could be detected by stimulation with other peptides shown in Tables 3a and 3b, despite those peptides had possible binding activity with HLA-A*0201. As a typical case of negative data, a specific CTL response was not observed from peptide-pulsed target cells stimulated with HJURP-A02-9-150 (SEQ ID NO: 25) (j). As a result, 9 peptides derived from HJURP were identified as having the potential to induce potent CTLs.

Establishment of CTL Lines and Clones Against HJURP Derived Peptides

The cells that showed peptide specific CTL activity detected by IFN-gamma ELISPOT assay in the well number #4 with HJURP-A02-9-496 (SEQ ID NO: 26) (a), in #4 with HJURP-A02-9-406 (SEQ ID NO: 30) (b), in #5 with HJURP-A02-9-129 (SEQ ID NO: 31) (c), in #5 with HJURP-A02-10-405 (SEQ ID NO: 37) (d) and in #3 with HJURP-A02-10-128 (SEQ ID NO: 38) (e) were expanded and CTL lines were established by limiting dilution as described in the "Materials and Methods" section above. CTL activity of those CTL lines was determined by IFN-gamma ELISA assay (FIGS. 6a-e). The CTL lines demonstrated potent IFN-gamma production against the target cells pulsed with the corresponding peptide as compared to target cells without peptide pulse.

Furthermore, the CTL clones were established by limiting dilution from the CTL line as described in "Materials and Methods", and IFN-gamma production from CTL clones against target cells pulsed peptide was determined by IFN-gamma ELISA assay. Potent IFN-gamma production were determined from CTL clones stimulated with HJURP-A02-9-406 (SEQ ID NO: 30) (a), HJURP-A02-9-129 (SEQ ID NO: 31) (b), HJURP-A02-10-405 (SEQ ID NO: 37) (c) and HJURP-A02-10-128 (SEQ ID NO: 38) (d) (FIGS. 7a-d).

Specific CTL Activity Against Target Cells Exogenously Expressing HJURP and HLA-A*0201

Figure 8:
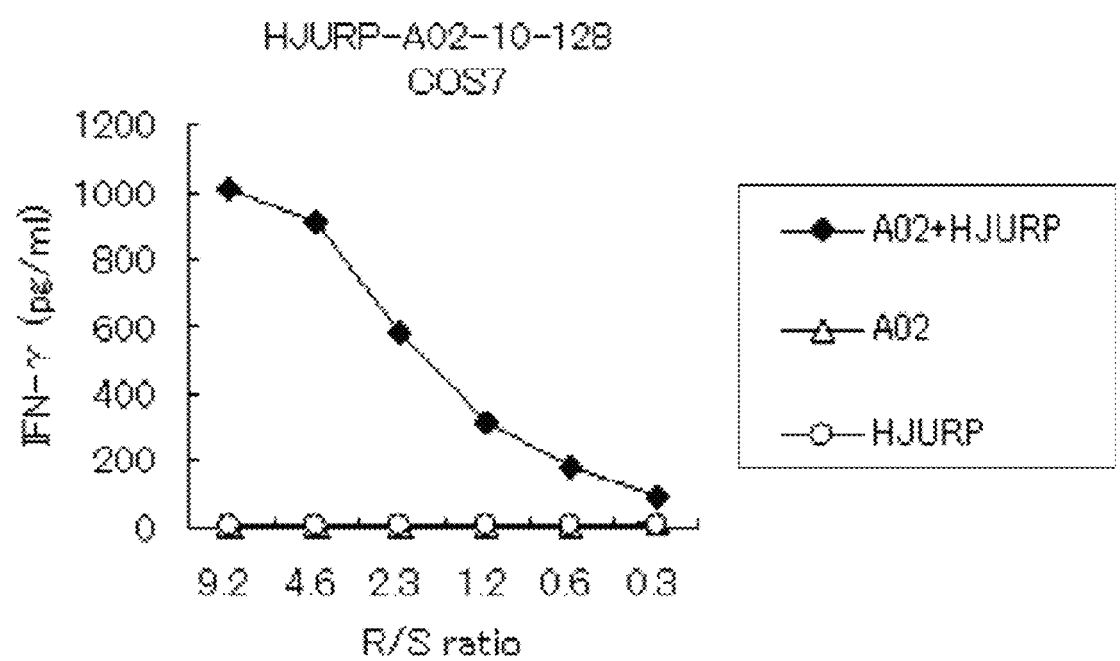
FIG. 8 is composed of a series of line graphs depicting specific CTL activity against the target cells that exogenously express HJURP and HLA-A*0201. COS7 cells transfected with HLA-A*0201 or the full length of HJURP gene were prepared as controls. The CTL clone established with HJURP-A02-10-128 (SEQ ID NO: 38) showed specific CTL activity against COS7 cells transfected with both HJURP and HLA-A*0201 (black lozenge). On the other hand, no significant specific CTL activity was detected against target cells expressing either HLA-A*0201 (triangle) or HJURP (circle).

The established CTL lines and clones raised against the peptide were examined for the ability to recognize target cells that endogenously express HJURP and HLA-A*0201 molecule. Specific CTL activity against COS7 cells which transfected with both the full length of HJURP and HLA-A*0201 molecule (a specific model for the target cells that endogenously express HJURP and HLA-A*0201 gene) were tested using the CTL clone raised by corresponding peptide as the effector cells. COS7 cells transfected with either full length of HJURP genes or HLA-A*0201 were prepared as controls. In FIG. 8, the CTL clone stimulated with HJURP-A02-10-128 (SEQ ID NO: 38) showed potent CTL activity against COS7 cells expressing both HJURP and HLA-A*0201. On the other hand, no significant specific CTL activity was detected against the controls. Thus, these data clearly demonstrated that peptides of HJURP-A02-10-128 (SEQ ID NO: 38) was endogenously processed and expressed on the target cells with HLA-A*0201 molecule and were recognized by the CTLs. These results indicate that this peptide derived from HJURP may be suitable as a cancer vaccine for the treatment of patients with HJURP expressing tumors.

Homology Analysis of Antigen Peptides

The CTLs stimulated with HJURP-A02-9-496 (SEQ ID NO: 26), HJURP-A02-9-354 (SEQ ID NO: 27), HJURP-A02-9-406 (SEQ ID NO: 30), HJURP-A02-9-129 (SEQ ID NO: 31), HJURP-A02-9-599 (SEQ ID NO: 32), HJURP-A02-9-386 (SEQ ID:35), HJURP-A02-10-405 (SEQ ID:37), HJURP-A02-10-128 (SEQ ID:38) and HJURP-A02-10-54 (SEQ ID NO: 43) showed significant and specific CTL activity. This result may be due to the fact that the sequences of HJURP-A02-9-496 (SEQ ID NO: 26), HJURP-A02-9-354 (SEQ ID NO: 27), HJURP-A02-9-406 (SEQ ID NO: 30), HJURP-A02-9-129 (SEQ ID NO: 31), HJURP-A02-9-599 (SEQ ID NO: 32), HJURP-A02-9-386 (SEQ ID:35), HJURP-A02-10-405 (SEQ ID:37), HJURP-A02-10-128 (SEQ ID:38) and HJURP-A02-10-54 (SEQ ID NO: 43) are homologous to peptides derived from other molecules that are known to sensitize the human immune system. To exclude this possibility, homology analyses were performed for these peptide sequences using as queries the BLAST algorithm (www.ncbi.nlm.nih.gov/blast/blast.cgi) which revealed no sequence with significant homology. The results of homology analyses indicate that the sequences of HJURP-A02-9-496 (SEQ ID NO: 26), HJURP-A02-9-354 (SEQ ID NO: 27), HJURP-A02-9-406 (SEQ ID NO: 30), HJURP-A02-9-129 (SEQ ID NO: 31), HJURP-A02-9-599 (SEQ ID NO: 32), HJURP-A02-9-386 (SEQ ID:35), HJURP-A02-10-405 (SEQ ID:37), HJURP-A02-10-128 (SEQ ID:38) and HJURP-A02-10-54 (SEQ ID NO: 43) are unique and thus, there is little possibility, to our best knowledge, that these molecules raise unintended immunologic response to some unrelated molecule.

In conclusion, novel HLA-A*0201 epitope peptides derived from HJURP were identified. The results herein demonstrate that the epitope peptide of HJURP may be suitable for use in for cancer immunotherapy.

INDUSTRIAL APPLICABILITY

The present invention provides new TAAs, particularly those derived from HJURP that induce potent and specific anti-tumor immune responses and have applicability to a wide variety of cancer types. Such TAAs can find use as peptide vaccines against diseases associated with HJURP, e.g., cancer, more particularly, AML, bladder cancer, breast cancer, cervical cancer, cholangiocellular carcinoma, CML, colorectal cancer, esophagus cancer, Diffused-type gastric cancer, liver cancer, NSCLC, lymphoma, osteosarcoma, ovarian cancer, pancreatic cancer, prostate cancer, renal carcinoma, SCLC, soft tissue tumor and testicular tumor.

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide of less than 15 amino acids having cytotoxic T lymphocyte (CTL) inducibility, wherein the peptide
comprises an amino acid sequence modified by substituting, deleting, inserting, or adding 1 or 2 amino acid residues to an amino acid sequence as shown in SEQ ID NO: 4.

2. The isolated peptide of claim 1, wherein the peptide has one or both of the following characteristics:
   (a) the second amino acid from the N-terminus of the amino acid sequence as shown in SEQ ID NO: 4 is selected from the group consisting of phenylalanine, methionine and tryptophan; and
   (b) the C-terminal amino acid of the amino acid sequence as shown in SEQ ID NO: 4 is selected from the group consisting of phenylalanine, leucine, isoleucine, and tryptophan.

3. The isolated peptide of claim 1, wherein said peptide is a nonapeptide or decapeptide.

4. A composition for inducing a CTL, wherein the composition comprises a peptide of less than 15 amino acids having cytotoxic T lymphocyte (CTL) inducibility, wherein the peptide is selected from the group consisting of:
   (a) an isolated peptide comprising an amino acid sequence as shown in SEQ ID NO: 4; and
   (b) an isolated peptide comprising an amino acid sequence modified by substituting, deleting, inserting, or adding 1 or 2 amino acid residues to an amino acid as shown in SEQ ID NO: 4
in combination with an adjuvant.

5. A pharmaceutical composition wherein the composition comprises a peptide of less than 15 amino acids having cytotoxic T lymphocyte (CTL) inducibility, wherein the peptide is selected from the group consisting of:
   (a) an isolated peptide comprising an amino acid sequence as shown in SEQ ID NO: 4; and
   (b) an isolated peptide comprising an amino acid sequence modified by substituting, deleting, inserting, or adding 1 or 2 amino acid residues to an amino acid as shown in SEQ ID NO: 4
in combination with an adjuvant.

6. A method for inducing an antigen-presenting cell (APC) with CTL inducibility, wherein the method comprises the step of contacting an APC with a peptide of less than 15 amino acids in vitro, ex vivo or in vivo, wherein the peptide is selected from the group consisting of:
   (a) an isolated peptide comprising an amino acid sequence as shown in SEQ ID NO: 4; and
   (b) an isolated peptide comprising an amino acid sequence modified by substituting, deleting, inserting, or adding 1 or 2 amino acid residues to an amino acid as shown in SEQ ID NO: 4.

7. A method for inducing a CTL by a method that comprises a step selected from the group consisting of:
   (i) co-culturing CD8 positive T cells with APCs that present on the surface a complex of an HLA antigen and a peptide; and
   (ii) co-culturing CD8 positive T cells with exosomes that present on the surface a complex of an HLA antigen and the peptide;
wherein the peptide is selected from the group consisting of:
   (a) an isolated peptide comprising an amino acid sequence as shown in SEQ ID NO: 4; and
   (b) an isolated peptide comprising an amino acid sequence modified by substituting, deleting, inserting, or adding 1 or 2 amino acid residues to an amino acid as shown in SEQ ID NO: 4.

8. The composition of claim 4, wherein the peptide consists of the amino acid sequence as shown in SEQ ID NO: 4.

9. The pharmaceutical composition of claim 5, wherein the peptide consists of the amino acid sequence as shown in SEQ ID NO: 4.

* * * * *

SEQUENCE LISTING

```
<160> NUMBER OF SEQ ID NOS: 54

<210> SEQ ID NO 1
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 1

Lys Tyr Leu Thr Gln Val Asp Ile Leu
1               5

<210> SEQ ID NO 2
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 2

Arg Tyr Asp Glu Ile Lys Glu Glu Phe
1               5

<210> SEQ ID NO 3
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 3
```

```
Arg Phe Gln Arg Arg Met Gln Arg Leu
1               5

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 4

Leu Tyr Ala Gly Met Leu His Ser Met
1               5

<210> SEQ ID NO 5
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 5

Arg Phe Arg Thr Leu Lys Trp Leu Ile
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 6

Ile Tyr Phe Asp Ser Ser Ala Thr Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 7

Lys Trp Leu Ile Ser Pro Val Lys Ile
1               5

<210> SEQ ID NO 8
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 8

Val Gln Gly Asn Ser Ser Gly Ile Phe
1               5

<210> SEQ ID NO 9
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 9
```

Ser Ser Ile Ile Ser Thr Lys Thr Phe
1               5

<210> SEQ ID NO 10
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 10

Lys Tyr Leu Thr Gln Val Asp Ile Leu Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 11

Thr Tyr Asn Leu Asp Glu Glu Asn Arg Phe
1               5                   10

<210> SEQ ID NO 12
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 12

Ser Tyr Arg Met Glu Glu Lys Ser Asp Phe
1               5                   10

<210> SEQ ID NO 13
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 13

Thr Tyr Glu Thr Pro Gln Gly Leu Arg Ile
1               5                   10

<210> SEQ ID NO 14
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 14

Lys Tyr Cys Leu Lys Ser Pro Gly Gln Met
1               5                   10

<210> SEQ ID NO 15
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 15

Gly Phe Gln Lys Leu Pro Ser Ser Pro Leu

```
<210> SEQ ID NO 16
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 16

Tyr Phe Asp Ser Ser Ala Thr Tyr Asn Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 17

Arg Phe Gln Arg Arg Met Gln Arg Leu Ile
1               5                   10

<210> SEQ ID NO 18
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 18

Lys Tyr Ser Ser Leu Ile Tyr Phe Asp Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 19

Val Thr Pro Ser Lys Tyr Ser Ser Leu Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 20

Ser Leu Gln Glu Thr Ser Ser Ser Ser Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 21

Leu His Pro Ser Ser Thr Asp Met Ala Leu
1               5                   10
```

```
<210> SEQ ID NO 22
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 22

Ile Tyr Phe Asp Ser Ser Ala Thr Tyr Asn
1               5                   10

<210> SEQ ID NO 23
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 23

Glu Tyr Phe Glu Cys Ala Gly Asn Arg Ala
1               5                   10

<210> SEQ ID NO 24
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 24

Leu Asn Pro Asp Pro His Phe Gln Gly Phe
1               5                   10

<210> SEQ ID NO 25
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 25

Tyr Leu Thr Gln Val Asp Ile Leu Leu
1               5

<210> SEQ ID NO 26
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 26

Ser Leu Ser Glu Ala Phe Glu Asn Leu
1               5

<210> SEQ ID NO 27
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 27

Lys Leu Glu Lys Ala Phe Leu Glu Val
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 28

Gly Met Leu His Ser Met Ser Arg Leu
1               5

<210> SEQ ID NO 29
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 29

Gln Met Ala Thr Leu Thr Tyr Glu Thr
1               5

<210> SEQ ID NO 30
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 30

Thr Leu Lys Trp Leu Ile Ser Pro Val
1               5

<210> SEQ ID NO 31
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 31

Val Ala Trp Ala Leu Ala Pro Ala Val
1               5

<210> SEQ ID NO 32
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 32

Met Thr Val Pro Leu Cys Ile Gly Val
1               5

<210> SEQ ID NO 33
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 33

Ala Leu Val Pro Arg Asn Asp Ser Leu
1               5
```

-continued

```
<210> SEQ ID NO 34
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 34

Leu Leu Ser Thr Lys Pro Ser Ser Ile
1               5

<210> SEQ ID NO 35
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 35

Ser Leu Ile Tyr Phe Asp Ser Ser Ala
1               5

<210> SEQ ID NO 36
<211> LENGTH: 9
<212> TYPE: PRT
<213> ORGANISM: Artificial Sequence
<220> FEATURE:
<223> OTHER INFORMATION: An artificially synthesized peptide sequence

<400> SEQUENCE: 36

Phe Leu Ser Ser Gln Pro Phe Glu Asp
1               5

<210> SEQ ID NO 37
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 37

Arg Thr Leu Lys Trp Leu Ile Ser Pro Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 38

Ser Val Ala Trp Ala Leu Ala Pro Ala Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 39

Ser Leu Leu Gly Ser Thr Ala Ile Glu Ala
1               5                   10

<210> SEQ ID NO 40
```

```
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 40

Arg Leu Leu Ser Thr Lys Pro Ser Ser Ile
1               5                   10

<210> SEQ ID NO 41
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 41

Gly Met Leu His Ser Met Ser Arg Leu Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 42

Gln Met Thr Val Pro Leu Cys Ile Gly Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 43

Thr Leu Thr Tyr Glu Thr Pro Gln Gly Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 44

Arg Met Glu Glu Lys Ser Asp Phe Met Leu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 45

Asn Leu Asp Glu Glu Asn Arg Phe Arg Thr
1               5                   10

<210> SEQ ID NO 46
<211> LENGTH: 10
```

```
<212> TYPE: PRT
<213> ORGANISM: Artificial Sequence
<220> FEATURE:
<223> OTHER INFORMATION: An artificially synthesized peptide sequence

<400> SEQUENCE: 46

Leu Leu Gln Gly Ala Glu Tyr Phe Glu Cys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 47

Arg Met Cys Leu Pro Asp Ser Trp Ala Met
1               5                   10

<210> SEQ ID NO 48
<211> LENGTH: 10
<212> TYPE: PRT
<213> ORGANISM: Artificial Sequence
<220> FEATURE:
<223> OTHER INFORMATION: An artificially synthesized peptide sequence

<400> SEQUENCE: 48

Ile Leu Leu Gln Gly Ala Glu Tyr Phe Glu
1               5                   10

<210> SEQ ID NO 49
<211> LENGTH: 3065
<212> TYPE: DNA
<213> ORGANISM: Homo sapiens

<400> SEQUENCE: 49
ctatttgagt tgtggcgcg cgaggccctg cagtccgggt tggcgcttgg gtactggctg        60
ggtccgatgc tgggtacgct gcgcgccatg gagggcgagg acgtggaaga cgaccagctg       120
ctgcagaagc tcagggccag tcgccgccgc ttccagaggc gcatgcagcg gctgatagag       180
aagtacaacc agcccttcga ggacaccccg gtggtgcaaa tggccacgct gacctacgag       240
acgccacagg gattgagaat ttggggtgga agactaataa aggaaagaaa cgaaggagag       300
atccaggact cctccatgaa gcccgcggac aggacagatg ctccgtgca agctgcagcc        360
tggggtcctg agcttccctc gcaccgcaca gtcctgggag ccgattcaaa agcggtgag        420
gtcgatgcca cgtcagacca ggaagagtca gttgcttggg ccttagcacc tgcagtgcct       480
caaagccctt tgaaaaatga attaagaagg aaatacttga cccaagtgga tatactgcta       540
caaggtgcag agtattttga gtgtgcaggt aacagagctg aagggatgt acgtgtgact        600
ccgctgcctt cactggcctc acctgccgtg cctgccccg atactgcag tcgtatctcc         660
agaaagagtc ctggtgaccc agcgaaacca gcttcatctc ccagagaatg ggatccttg        720
catccttcct ccacagacat ggccttagta cctagaaatg acagcctctc cctacaagag       780
accagtagca gcagcttctt aagcagccag cccctttgaag atgatgacat tgcaatgtg       840
accatcagtg acctgtacgc agggatgctg cactccatga gccggctgtt gagcacaaag       900
ccatcaagca tcatctccac caaaacgttc atcatgcaaa actggaactc caggaggagg       960
cacagatata agagcaggat gaacaaaaca tattgcaaag gagccagacg ttctcagagg      1020
agctccaagg agaacttcat accctgctct gagcctgtga aagggacagg ggcattaaga      1080
```

```
gattgcaaga acgtattaga tgtttcttgc cgtaagacag gtttaaaatt ggaaaaagct   1140
tttcttgaag tcaacagacc ccaaatccat aagttagatc caagttggaa ggagcgcaaa   1200
gtgacaccct cgaagtattc ttccttgatt tacttcgact ccagtgcaac atataatctt   1260
gatgaggaaa atagatttag gacattaaaa tggttaattt ctcctgtaaa aatagtttcc   1320
agaccaacaa tacgacaggg ccatggagag aaccgtcaga gggagattga aatccgattt   1380
gatcagcttc atcgggaata ttgcctgagt cccaggaacc agcctcgccg gatgtgcctc   1440
ccggactcct gggccatgaa catgtacaga gggggtcctg cgagtcctgg tggccttcag   1500
ggcttagaaa cccgcaggct gagtttacct tccagcaaag caaaagcaaa agtttaagt    1560 gaggcttttg aaaacctagg caaaagatct ctggaagcag gtaggtgcct gcccaagagc   1620
gattcatctt catcacttcc aaagaccaac cccacacaca gcgcaactcg cccgcagcag   1680
acatctgacc ttcacgttca gggaaatagt tctggaatat ttagaaagtc agtgtcaccc   1740
agcaaaactc tttcagtccc agataaagaa gtgccaggcc acggaaggaa tcgttacgat   1800
gaaattaaag aagaatttga caagcttcat caaaagtatt gcctcaaatc tcctgggcag   1860
atgacagtgc ctttatgtat tggagtgtct acagataaag caagtatgga agttcgatat   1920
caaacagaag gcttcttagg aaaattaaat ccagaccctc acttccaggg tttccagaag   1980
ttgccatcat caccctggg gtgcagaaaa agtctactgg gctcaactgc aattgaggct    2040
ccttcatcta catgtgttgc tcgtgccatc acgagggatg gcacgaggga ccatcagttc   2100
cctgcaaaaa gacccaggct atcagaaccc cagggctccg gacgccaggg caattccctg   2160
ggtgcctcag atggggtgga caacaccgtc agaccgggag accagggcag ctcttcacag   2220
cccaactcag aagagagagg agagaacacg tcttacagga tggaagagaa aagtgatttc   2280
atgctagaaa aattggaaac taaaagtgtg tagctaggtt atttcggagt gttatttatc    2340
ttcccacttg ctctctgttt gtattttgt tttgttttg attcttgaga ctgtgaggac      2400
ttggttgact tctctgccct taaagtaaat attagtgaaa ttggttccat cagagataac   2460
ctcgagttct tggtgtagaa attatgtgaa taaagttgct caattagaat ttttaggggtt   2520 ctctttgata ggcctgtttt tctgatgtgt gtgtttttt tggggggggg ttatttgttt     2580
gtttgtttgt ttgtttgttt gttttttgaga cagtctctct ctatcgccca ggctggagtg   2640
cggtggcaca atcttggctc actgcaactt ccgcctcccg ggttcaagcg attcttctgc    2700
ctcagcctcc cgagtagctg ggattacagg cgcgcgccac cacgcctggc taattttttgt   2760 agttttagta gagacggggt ttcaccatat tgaccaggct ggtctcgagc tcctggcctc    2820
gtgatccatc tgcctcggcc tcccaaagtg ctgggattat aggcgtgagc cactgctccc    2880
agccgtgtgt tcttttttaa atttagatat gtccagagaa tcctctctcc tgtttcccat    2940
ttcattcgag aatattgttt gcttgtgaga cgtaagttcg agccctgcat gcaatgaccc    3000
ttgaaggaaa ataaacagtc ctggtggtcc cagacgctcc tgcagccaca aaaaaaaaa    3060 aaaaa                                                               3065
```

<210> SEQ ID NO 50
<211> LENGTH: 748
<212> TYPE: PRT
<213> ORGANISM: Homo sapiens

<400> SEQUENCE: 50

Met Leu Gly Thr Leu Arg Ala Met Glu Gly Glu Asp Val Glu Asp Asp
1               5                   10                  15

-continued

Gln Leu Leu Gln Lys Leu Arg Ala Ser Arg Arg Phe Gln Arg Arg
            20                  25                  30

Met Gln Arg Leu Ile Glu Lys Tyr Asn Gln Pro Phe Glu Asp Thr Pro
        35                  40                  45

Val Val Gln Met Ala Thr Leu Thr Tyr Glu Thr Pro Gln Gly Leu Arg
    50                  55                  60

Ile Trp Gly Gly Arg Leu Ile Lys Glu Arg Asn Glu Gly Glu Ile Gln
65                  70                  75                  80

Asp Ser Ser Met Lys Pro Ala Asp Arg Thr Asp Gly Ser Val Gln Ala
                85                  90                  95

Ala Ala Trp Gly Pro Glu Leu Pro Ser His Arg Thr Val Leu Gly Ala
            100                 105                 110

Asp Ser Lys Ser Gly Glu Val Asp Ala Thr Ser Asp Gln Glu Glu Ser
        115                 120                 125

Val Ala Trp Ala Leu Ala Pro Ala Val Pro Gln Ser Pro Leu Lys Asn
    130                 135                 140

Glu Leu Arg Arg Lys Tyr Leu Thr Gln Val Asp Ile Leu Leu Gln Gly
145                 150                 155                 160

Ala Glu Tyr Phe Glu Cys Ala Gly Asn Arg Ala Gly Arg Asp Val Arg
                165                 170                 175

Val Thr Pro Leu Pro Ser Leu Ala Ser Pro Ala Val Pro Ala Pro Gly
            180                 185                 190

Tyr Cys Ser Arg Ile Ser Arg Lys Ser Pro Gly Asp Pro Ala Lys Pro
        195                 200                 205

Ala Ser Ser Pro Arg Glu Trp Asp Pro Leu His Pro Ser Ser Thr Asp
    210                 215                 220

Met Ala Leu Val Pro Arg Asn Asp Ser Leu Ser Leu Gln Glu Thr Ser
225                 230                 235                 240

Ser Ser Ser Phe Leu Ser Ser Gln Pro Phe Glu Asp Asp Ile Cys
                245                 250                 255

Asn Val Thr Ile Ser Asp Leu Tyr Ala Gly Met Leu His Ser Met Ser
                260                 265                 270

Arg Leu Leu Ser Thr Lys Pro Ser Ser Ile Ile Ser Thr Lys Thr Phe
        275                 280                 285

Ile Met Gln Asn Trp Asn Ser Arg Arg His Arg Tyr Lys Ser Arg
    290                 295                 300

Met Asn Lys Thr Tyr Cys Lys Gly Ala Arg Arg Ser Gln Arg Ser Ser
305                 310                 315                 320

Lys Glu Asn Phe Ile Pro Cys Ser Glu Pro Val Lys Gly Thr Gly Ala
                325                 330                 335

Leu Arg Asp Cys Lys Asn Val Leu Asp Val Ser Cys Arg Lys Thr Gly
            340                 345                 350

Leu Lys Leu Glu Lys Ala Phe Leu Glu Val Asn Arg Pro Gln Ile His
        355                 360                 365

Lys Leu Asp Pro Ser Trp Lys Glu Arg Lys Val Thr Pro Ser Lys Tyr
    370                 375                 380

Ser Ser Leu Ile Tyr Phe Asp Ser Ser Ala Thr Tyr Asn Leu Asp Glu
385                 390                 395                 400

Glu Asn Arg Phe Arg Thr Leu Lys Trp Leu Ile Ser Pro Val Lys Ile
                405                 410                 415

Val Ser Arg Pro Thr Ile Arg Gln Gly His Gly Glu Asn Arg Gln Arg
            420                 425                 430

-continued

```
Glu Ile Glu Ile Arg Phe Asp Gln Leu His Arg Glu Tyr Cys Leu Ser
            435                 440                 445
Pro Arg Asn Gln Pro Arg Met Cys Leu Pro Asp Ser Trp Ala Met
450                 455                 460
Asn Met Tyr Arg Gly Gly Pro Ala Ser Pro Gly Gly Leu Gln Gly Leu
465                 470                 475                 480
Glu Thr Arg Arg Leu Ser Leu Pro Ser Ser Lys Ala Lys Ala Lys Ser
                485                 490                 495
Leu Ser Glu Ala Phe Glu Asn Leu Gly Lys Arg Ser Leu Glu Ala Gly
                500                 505                 510
Arg Cys Leu Pro Lys Ser Asp Ser Ser Ser Leu Pro Lys Thr Asn
            515                 520                 525
Pro Thr His Ser Ala Thr Arg Pro Gln Gln Thr Ser Asp Leu His Val
            530                 535                 540
Gln Gly Asn Ser Ser Gly Ile Phe Arg Lys Ser Val Ser Pro Ser Lys
545                 550                 555                 560
Thr Leu Ser Val Pro Asp Lys Glu Val Pro Gly His Gly Arg Asn Arg
                565                 570                 575
Tyr Asp Glu Ile Lys Glu Glu Phe Asp Lys Leu His Gln Lys Tyr Cys
                580                 585                 590
Leu Lys Ser Pro Gly Gln Met Thr Val Pro Leu Cys Ile Gly Val Ser
            595                 600                 605
Thr Asp Lys Ala Ser Met Glu Val Arg Tyr Gln Thr Glu Gly Phe Leu
            610                 615                 620
Gly Lys Leu Asn Pro Asp Pro His Phe Gln Gly Phe Gln Lys Leu Pro
625                 630                 635                 640
Ser Ser Pro Leu Gly Cys Arg Lys Ser Leu Leu Gly Ser Thr Ala Ile
                645                 650                 655
Glu Ala Pro Ser Ser Thr Cys Val Ala Arg Ala Ile Thr Arg Asp Gly
                660                 665                 670
Thr Arg Asp His Gln Phe Pro Ala Lys Arg Pro Arg Leu Ser Glu Pro
            675                 680                 685
Gln Gly Ser Gly Arg Gln Gly Asn Ser Leu Gly Ala Ser Asp Gly Val
            690                 695                 700
Asp Asn Thr Val Arg Pro Gly Asp Gln Gly Ser Ser Ser Gln Pro Asn
705                 710                 715                 720
Ser Glu Glu Arg Gly Glu Asn Thr Ser Tyr Arg Met Glu Glu Lys Ser
                725                 730                 735
Asp Phe Met Leu Glu Lys Leu Glu Thr Lys Ser Val
            740                 745
```

<210> SEQ ID NO 51
<211> LENGTH: 22
<212> TYPE: DNA
<213> ORGANISM: Artificial Sequence
<220> FEATURE:
<223> OTHER INFORMATION: 5'R synthesized primer

<400> SEQUENCE: 51
gtctaccagg cattcgcttc at                                              22

<210> SEQ ID NO 52
<211> LENGTH: 24
<212> TYPE: DNA
<213> ORGANISM: Artificial Sequence
<220> FEATURE:
<223> OTHER INFORMATION: 3' synthesized primer for TH alpha-C

```
<400> SEQUENCE: 52
tcagctggac cacagccgca gcgt                                          24

<210> SEQ ID NO 53
<211> LENGTH: 21
<212> TYPE: DNA
<213> ORGANISM: Artificial Sequence
<220> FEATURE:
<223> OTHER INFORMATION: 3' synthesized primer for TR beta-C1

<400> SEQUENCE: 53
tcagaaatcc tttctcttga c                                             21

<210> SEQ ID NO 54
<211> LENGTH: 24
<212> TYPE: DNA
<213> ORGANISM: Artificial Sequence
<220> FEATURE:
<223> OTHER INFORMATION: 3' synthesized primer for TR beta-C2

<400> SEQUENCE: 54
ctagcctctg gaatcctttc tctt                                          24
```